US007741440B2

(12) United States Patent
Noteborn et al.

(10) Patent No.: US 7,741,440 B2
(45) Date of Patent: Jun. 22, 2010

(54) APOPTIN-ASSOCIATING PROTEIN

(75) Inventors: Mathieu Hubertus M. Noteborn, Leiderdorp (NL); Astrid Adriana A. M. Danen-van Oorschot, Berkel en Rodenrijs (NL); Jennifer Leigh Rohn, Amsterdam (NL); Bertram Weiss, Berlin (DE); Luisella Toschi, Berlin (DE)

(73) Assignee: Leadd B.V., Leiden (NL)

( * ) Notice: Subject to any disclaimer, the term of this patent is extended or adjusted under 35 U.S.C. 154(b) by 174 days.

(21) Appl. No.: 11/879,370

(22) Filed: Jul. 16, 2007

(65) Prior Publication Data

US 2008/0058267 A1 Mar. 6, 2008

Related U.S. Application Data

(62) Division of application No. 09/733,416, filed on Dec. 8, 2000, now Pat. No. 7,256,274.

(30) Foreign Application Priority Data

Dec. 10, 1999 (EP) ................... 99204242
Apr. 7, 2000 (EP) ................... 00250119

(51) Int. Cl.
C07K 14/00 (2006.01)
C07H 21/04 (2006.01)

(52) U.S. Cl. .................... 530/350; 536/23.1
(58) Field of Classification Search ............ None
See application file for complete search history.

(56) References Cited

U.S. PATENT DOCUMENTS

| 5,491,073 | A | 2/1996 | Noteborn et al. | |
| 5,981,205 | A | 11/1999 | Hemmings et al. | |
| 6,809,189 | B2 | 10/2004 | Noteborn et al. | |
| 6,878,692 | B2 | 4/2005 | Noteborn et al. | |
| 7,151,161 | B1* | 12/2006 | Carulli et al. | 530/350 |
| 7,256,274 | B2* | 8/2007 | Noteborn et al. | 536/23.1 |
| 2003/0105315 | A1 | 6/2003 | Specht et al. | |
| 2008/0103099 | A1* | 5/2008 | Noteborn et al. | 514/12 |

FOREIGN PATENT DOCUMENTS

| EP | 0921192 A1 | 6/1999 |
| EP | 0924296 A2 | 6/1999 |
| EP | 1 106 691 A1 | 12/1999 |
| EP | 1 111 045 A2 | 12/2000 |
| EP | 1 111 045 A3 | 12/2000 |
| WO | WO 96/41191 | 12/1996 |
| WO | WO 98/39448 | 9/1998 |
| WO | WO 98/46760 | 10/1998 |
| WO | WO 99/08108 | 2/1999 |
| WO | WO 99/28460 | 6/1999 |
| WO | WO 99/28461 | 6/1999 |
| WO | WO 01/42461 A3 | 6/2001 |

OTHER PUBLICATIONS

Orkin and Motulsky NIH ad hoc committee Dec. 1995 http://www.nih.gov/news/pane/rep.html.*
Theodore Friedmann (Scientific American Jun. 1997, p. 96-101).*
Inder Verma (Nature Sep. 1997;389:239-242).*
Rubanyi (Molecular Aspects of Medecine 2001 ;22:113-142).*
Suzuki et al (Gene Oct. 24, 1997;200(1-2):149-56) Abstract Only.*
Zhuang et al., Apoptin, a Protein Derived from Chicken Anemia Virus, Induces p53-independent Apoptosis in Human Osteosarcoma Cells, Cancer Res, Feb. 1995, pp. 486-489, vol. 55, No. 3.
Pietersen et al., Specific tumor-cell killing with adenovirus vectors containing the apoptin gene, Gene Therapy, 1999, pp. 882-892, vol. 6.
Bellamy et al., "Cell death in health and disease: the biology and regulation of apoptosis," Seminars in Cancer Biology, vol. 6, pp. 3-16 (1995).
Danen-van Oorschot et al., "Apoptin induces apoptosis in human transformed and malignant cells but not in normal cells." Proc. Nat'l. Acad Sci. USA vol. 94, pp. 5843-5847 (May 1997).
Danen-van Oorschot et al., "BAG-1 inhibits p53-induced but not apoptin-induced apoptosis," Apoptosis, vol. 2, No. 4, pp. 395-402 (1997).
Duke et al, "Cell Suicide in Health and Disease," Scientific American, pp. 80-87 (Dec. 1996).
Noteborn et al., "A Single Chicken Anemia Virus Protein Induces Apoptosis," Journal of Virology, vol. 68, No. 1, pp. 346-351 (Jan. 1994).
Noteborn et al., "Characterization of Cloned Chicken Anemia Virus DNA That Contains All Elements for the Infectious Replication Cycle." Journal of Virology, vol. 65, No. 6, pp. 3131-3139 (Jun. 1991).
Noteborn et al, "Chicken Anemia Virus Induction of Apoptosis by a Single Protein of a Single-Stranded DNA Virus," Seminars in Virology. vol. 8, pp. 497-504 (1998).
Noteborn et al., "Simultaneous expression of recombinant baculovirus-encoded chicken anaemia virus (CAV) proteins VP1 and VP2 is required for formation of the CAV-specific neutralizing epitope," Journal of General Virology, vol. 79, pp. 3073-3077 (1998).
Steller Hermann, "Mechanisms and Genes of Cellular Suicide," Science, vol. 267, pp. 1445-1449 (Mar. 10, 1995).
Teodoro et al , "Regulation of Apoptosis by Viral Gene Products," Journal of Virology, vol. 71, No. 3, pp. 1739-1746 (Mar. 1997).
Thompson, "Apoptosis in the Pathogenesis and Treatment of Disease," Science, vol. 267, pp. 1456-1462 (Mar. 10, 1995).
Strausberg, "qy85c09.x1 NCI_CGAP_Brn25 *Homo sapiens* cDNA clone Image:2018800 3', mRNA sequence," Jan. 7, 1999, Accession No. AI360308.

(Continued)

*Primary Examiner*—Christopher H Yaen
(74) *Attorney, Agent, or Firm*—TraskBritt

(57) ABSTRACT

The invention relates to the field of apoptosis. The invention provides novel therapies, for example, novel combinatorial therapies or novel therapeutic compounds that can work alone, sequentially to, or jointly with Apoptin, especially in those cases wherein p53 is completely or partially non-functional.

14 Claims, 10 Drawing Sheets

OTHER PUBLICATIONS

Zhao, "Use of BAC End Sequences from Library RPCI-11 for Sequence-Ready Map building," Mar. 15, 1999, Accession No. AQ382839.

Strausberg, "wd70d04.x1 NCI_CGAP_Lu24 Homo sapiens cDNA clone IMAGE:2336935 3', mRNA sequence," Jun. 3, 1999, Accession No. AI692778.

Benet et al., pp. 3-32, in The Pharmacological Basis of Therapeutics, 8th ed., McGraw-Hill, Inc., New York, 1990.

Jain et al., Vascular and interstitial barriers to delivery of therapeutic agents in tumors, Cancer and Metastasis Reviews, 1990, pp. 253-266, vol. 9.

Jain, Delivery of Molecular Medicine to Solid Tumors, 1996, Science, pp. 1079-1080, vol. 271.

Dermer, Another Anniversary for the War on Cancer, Biotechnology, 1994, pp. 320, vol. 12.

Database GenEmbl on GenCore version 4.5, Accession No. AX015052, Oct. 1999.

Strausberg, Database EST on GenCore version 4.5, Accession No. BE746443, Sep. 2000.

Danen-van Oorschot et al., BCL-2 Stimulated Apoptin-induced Apoptosis, pp. 245-249 in Drug Resistance in Leukemia and Lymphoma III, ed. Kaspers et al., Kluwer Academic/Plenum Publishers, New York, 1999.

Noteborn et al., Apoptin-induced apoptosis: potential for antitumor therapy, Drug Resistance Updates, 1998, pp. 99-103, vol. 1.

Noteborn et al., Apoptin induces apoptosis in transformed cells specifically: Potentials for an antitumor therapy, Biogenic Amines, 1998, pp. 73-91, vol. 15, No. 1.

Abstract XP-002140967, May 1999.

Abstract XP-002140968, May 1995.

Abstract XP-002140969, 2000.

McDonnell et al., "Implications of apoptotic cell death regulation in cancer therapy," Cancer Biology, 1995, pp. 53-60.

Mullersman et al., "The PHD finger: implications for chromatin-mediated transcriptional regulation," TIBS 20, Feb. 1995, pp. 56-59.

Jacobson et al., "Modifying chromatin and concepts of cancer," Chromosomes and expression mechanisms, pp. 175-184.

Lu et al., "A Novel Gene (PLU-1) Containing Highly Conserved Putative DNA/Chromatin Binding Motifs Is Specifically Up-regulated in Breast Cancer," The Journal of Biological Chemistry, 1999, pp. 15633-15645, vol. 274, No. 22.

Zhuang et al., "Apoptin, a Protein Encoded by Chicken Anemia Virus, Induces Cell Death in Various Human Hematologic Malignant Cells in vitro," Leukemia, vol. 9, Suppl. 1, pp. S118-S120, 1995.

Danen-van Oorschot et al., Apoptin induces apoptosis in human transformed and malignant cells but no in normal cells, Proc Natl Acad Sci, 1997, pp. 5843-5847, vol. 94, USA.

Danen-van Oorschot et al., BAG-1 inhibits p53-induced but not apoptin-induced apoptosis, Apoptosis, 1997, pp. 395-402, vol. 2.

Garcia et al., RYBP, a new repressor protein that interacts with components of the mammalian polycomb complex, and with the transcription factor YY1, EMBO J, 1999, pp. 3404-3418, vol. 18.

Kerr, et al., Apoptosis: Its significance in cancer and cancer therapy, Cancer, 1994, pp. 2013-2026, vol. 73.

Levine, p53, the cellular gatekeeper for growth and division, Cell, 1997, pp. 323-331, vol. 88.

Paulovich et al., When checkpoints fail, Cell, 1997, pp. 315-321, vol. 88.

Strausberg, qt26b07.x1 Soares_pregnant_uterus_NbHPU Homo sapiens cDNA clone, EMBL Database; Accession No. A1342119, Mar. 31, 1998, XP002140933.

Overbeek, Transgenic Animal Technology, 1994, pp. 96-98.

Wall, Theriogenology, 1996, pp. 57-68, vol. 45.

Houdebine, J. Biotech, 1994, pp. 269-287, vol. 34.

Kappell, Current Opin Biotech, 1992, pp. 548-553, vol. 3.

Cameron et al., Mol. Biol. 1997, pp. 253-265, vol. 7.

Niemann, Trans Res. 1997, pp. 73-75, vol. 7.

Mullins, Hypertension, 1993, pp. 630-633, vol. 22.

Mullins, Nature, 1990, pp. 541-544, vol. 344.

Hammer, Cell, 1990, pp. 1099-1112, vol. 63.

Mullins, EMBO J. 1989, pp. 4065-4072, vol. 8.

Taurog, J. Immunol, 1988, pp. 4020-4023, vol. 141.

Mullins, J. Clin. Invest. 1996, pp. S37-S40, vol. 98.

Zachariae et al., Science, Nov. 1996, pp. 1201-1204, vol. 274.

Teodoro et al., Genes Dev., Aug. 15, 2004, pp. 1952-1957, vol. 18, No. 16.

Crystal, R.G., Science, Oct. 1995, pp. 404-410, vol. 270.

Tait et al., Clin. Canc. Res., Jul. 1999, pp. 1708-1714, vol. 5.

Gura, Science, pp. 1041-1042, 1997, vol. 278.

Reiger et al., Glossary of Genetics and Cytogenetics, Classical and Molecular, 4th Ed., Springer-Verlay, Berlin, 1976.

Thompson, C.B., 1995, Apoptosis in the pathogenesis and treatment of disease, Science, 267, 1456-1462.

Jenuwein et al., Cell. Mol. Life Sci., 1998, pp. 80-93, vol. 54.

Rozovskaia et al., Oncogene, 2000, pp. 351-357, vol. 19.

Jacobson et al., Curr. Opinion in Gen. & Dev., 1999, pp. 175-184, vol. 9.

Lai et al., 2000, Identification of novel human genes evolutionarily conserved in Cernorhabditis elegans, Genome Res., 2000, pp. 703-713, vol. 10, No. 5.

Lai et al., Homo sapiens CGI-85 protein, EMBL Sequences Accession No. AF151843, Jun. 6, 1999.

* cited by examiner

*start AAP4 cDNA*

```
  1  GCCACGAAGG CCGGGAGAGC TCGCCCTGCA CCTACATAAC TCGGCGGTCA GTGAGGACAA
        adaptor
 61  GAACAAATCT GAAGGAGGCC TCTGACATCA AGCTTGAACC AAATACGTTG AATGGCTATA
121  AAAGCAGTGT GACGGAACCT TGCCCCGACA GTGGTGAACA GCTGCAGCCA GCTCCTGTGC
181  TGCAGGAGGA AGAACTGGCT CATGAGACTG CACAAAAAGG GGAGGCAAAG TGTCATAAGA
241  GTGACACAGG CATGTCCAAA AAGAAGTCAC GACAAGGAAA ACTTGTGAAA CAGTTTGCAA
301  AAATAGAGGA ATCTACTCCA GTGCACGATT CTCCTGGAAA AGACGACGCG GTACCAGATT
361  TGATGGGTCC CCATTCTGAC CAGGGTGAGC ACAGTGGCAC TGTGGGCGTG CCTGTGAGCT
421  ACACAGACTG TGCTCCTTCA CCCGTCGGTT GTTCAGTTGT GACATCAGAT AGCTTCAAAA
481  CAAAAGACAG CTTTAGAACT GCAAAAAAGT AAAAAGAAGA CGCGAATCAC AAGGTATGAT
541  GCACAGTTAA TCCTAGAAAA TAACTCTGGG AGTCCCAAAT TGACTCTTCG TAGGCGTCAT
601  GATAGCAGCA GCAAAACAAA TGGACCAAGA GAATGATGGG AATGAAACTC TTCCCAAAAT
661  TAAGCATCAA GTTTAAGCCA AAGACCATGA CAACGATAAC AATCTCGATG TAGCAAAGTT
721  ATAAGGGTTT AGCTCAGGAT TAGGAATGTT TCACAAAATT AAAAAGGCAT
```

(SEQ ID NO:10)

FIG. 1

```
1    HEGRESSPCT YITRRSVRTR TNLKEASDIK LEPNTLNGYK SSVTEPCPDS GEQLQPAPVL

61   QEEELAHETA QKGEAKCHKS DTGMSKKKSR QGKLVKQFAK IEESTPVHDS PGKDDAVPDL

121  MGPHSDQGEH SGTVGVPVSY TDCAPSPVGC SVVTSDSFKT KDSFRTAKK* KEEANHKV*C

181  TVNPRK*LWE SQIDSS*AS* *QQQNKWTKR MMGMKLFPKL SIKFKPKTMT TITISM*QSY

241  KGLAQD*ECF TKLKRH
```

(SEQ ID NO:12)

FIG. 2

AAP-4 and/or Apoptin induce apoptosis in human tumor cells

Apoptosis activity in Saos-2 and U2OS cells

|  | Synthesised proteins | | | |
|---|---|---|---|---|
|  | LacZ | AAP-4 | Apoptin | AAP-4/Apoptin |
| Exp.1 (Saos-2) | - | ++ | ++ | +++ |
| Exp.2 (Saos-2) | - | ++ | ++ | +++ |
| Exp.3 (Saos-2) | - | ++ | ++ | +++ |
| Exp.1 (U2OS) | - | ++ | ++ | ND |
| Exp.2 (U2OS) | - | ++ | ++ | ND |
| Exp.3 (U2OS) | - | ++ | ++ | ND |

ND not determined

FIG. 3

*: "circular" structures containing AAP-4 and apoptin

```
   1  CGGCAGGGCA GCGGGGCGAT GAGGTGAGGA CGCCCGGGAA CCGGAGGCGG
  51  CACCGCGCGG CGCACGGACC TGGGACGCGG AGTCCTGAAG CCGGCGGACG
 101  GTTTTCGTAC GGGCGGCCGT GCGCGAGGCG AGGAGAGAAC ATTGAAAGTA
 151  TTCTCTAAGC TATTTGAAGA GAGTGACTAA ATGCACCTGG GTCAGGCTGT
 201  CTGTGGGTAT GAAGTGGTTG GGAGAATCCA AGAACATGGT GGTGAATGGC
 251  AGGAGAAATG GAGGCAAGTT GTCTAATGAC CATCAGCAGA ATCAATCAAA
 301  ATTACAGCAC ACGGGGAAGG ACACCCTGAA GGCTGGCAAA AATGCAGTCG
 351  AGAGGAGGTC GAACAGATGT AATGGTAACT CGGGATTTGA AGGACAGAGT
 401  CGCTATGTAC CATCCTCTGG AATGTCCGCC AAGGAACTCT GTGAAAATGA
 451  TGACCTAGCA ACCAGTTTGG TTCTTGATCC CTATTTAGGT TTTCAAACAC
 501  ACAAAATGAA TACTAGCGCC TTTCCTTCGA GGAGCTCAAG GCATTTTTCA
 551  AAATCTGACA GTTTTCTCA CAACAACCCT GTGAGATTTA GGCCTATTAA
 601  AGGAAGGCAG GAAGAACTAA AGGAAGTAAT TGAACGTTTT AAGAAAGATG
 651  AACACTTGGA GAAAGCCTTC AAATGTTTGA CTTCAGGCGA ATGGGCACGG
 701  CACTATTTTC TCAACAAGAA TAAAATGCAG GAGAAATTAT TCAAAGAACA
 751  TGTATTTATT TATTTGCGAA TGTTTGCAAC TGACAGTGGA TTTGAAATAT
 801  TGCCATGTAA TAGATACTCA TCAGAACAAA ATGGAGCCAA AATAGTTGCA
 851  ACAAAAGAGT GGAAACGAAA TGACAAAATA GAATTACTGG TGGGTTGTAT
 901  TGCCGAACTT TCAGAAATTG AGGAGAACAT GCTACTTAGA CATCCAGAAA
 951  ACGACTTCAG TGTCATGTAC TCCACAAGGA AAAACTGTGC TCAACTCTGG
1001  CTGGGTCCTG CTGCGTTTAT AAACCATGAT TGCAGACCTA ATTGTAAGTT
1051  TGTGTCAACT GGTCGAGATA CAGCATGTGT GAAGGCTCTA AGAGACATTG
1101  AACCTGGAGA AGAAATTTCT TGTTATTATG GAGATGGGTT CTTTGGAGAA
1151  AATAATGAGT TCTGCGAGTG TTACACTTGC GAAAGACGGG GCACTGGTGC
1201  TTTTAAATCC AGAGTGGGAC TGCCTGCGCC TGCTCCTGTT ATCAATAGCA
1251  AATATGGACT CAGAGAAACA GATAAACGTT TAAATAGGCT TAAAAAGTTA
1301  GGTGACAGCA GCAAAAATTC AGACAGTCAA TCTGTCAGCT CTAACACTGA
1351  TGCAGATACC ACTCAGGAAA AAACAATGC AACTTCTAAC CGAAAATCTT
1401  CAGTTGGCGT AAAAAAGAAT AGCAAGAGCA GAACGTTAAC GAGGCAATCT
```

FIG. 5A

1451 ATGTCAAGAA TTCCAGCTTC TTCCAACTCT ACCTCATCTA AGCTAACTCA

1501 TATAAATAAT TCCAGGGTAC CAAAGAAACT GAAGAAGCCT GCAAAGCCTT

1551 TACTTTCAAA GATAAAATTG AGAAATCATT GCAAGCGGCT GGAGCAAAAG

1601 AATGCTTCAA GAAAACTCGA ATGGGAAAC TTAGTACTGA AGAGCCTAA

1651 AGTAGTTCTG TATAAAAATT TGCCCATTAA AAAGATAAG GAGCCAGAGG

1701 GACCAGCCCA AGCCGCAGTT GCCAGCGGGT GCTTGACTAG ACACGCGGCG

1751 AGAGAACACA GACAGAATCC TGTGAGAGGT GCTCATTCGC AGGGGAGAG

1801 CTCGCCCTGC ACCTACATAA CTCGGCGGTC AGTGAGGACA GAACAAATC

1851 TGAAGGAGGC CTCTGACATC AAGCTTGAAC CAAATACGTT GAATGGCTAT

1901 AAAAGCAGTG TGACGGAACC TTGCCCCGAC AGTGGTGAAC AGCTGCAGCC

1951 AGCTCCTGTG CTGCAGGAGG AAGAACTGGC TCATGAGACT GCACAAAAAG

2001 GGGAGGCAAA GTGTCATAAG AGTGACACAG GCATGTCCAA AAAGAAGTCA

2051 CGACAAGGAA AACTTGTGAA ACAGTTTGCA AAAATAGAGG AATCTACTCC

2101 AGTGCACGAT TCTCCTGGAA AAGACGACGC GGTACCAGAT TTGATGGGTC

2151 CCCATTCTGA CCAGGGTGAG CACAGTGGCA CTGTGGGCGT GCCTGTGAGC

2201 TACACAGACT GTGCTCCTTC ACCCGTCGGT TGTTCAGTTG TGACATCAGA

2251 TAGCTTCAAA ACAAAAGACA GCTTTAGAAC TGCAAAAAGT AAAAAGAAGA

2301 GGCGAATCAC AAGGTATGAT GCACAGTTAA TCCTAGAAAA TAACTCTGGG

2351 ATTCCCAAAT TGACTCTTCG TAGGCGTCAT GATAGCAGCA GCAAAACAAA

2401 TGACCAAGAG AATGATGGAA TGAACTCTTC CAAAATAAGC ATCAAGTTAA

2451 GCAAAGACCA TGACAACGAT AACAATCTCT ATGTAGCAAA GCTTAATAAT

2501 GGATTTAACT CAGGATCAGG CAGTAGTTCT ACAAAATTAA AAATCCAGCT

2551 AAAACGAGAT GAGGAAAATA GGGGGTCTTA TACAGAGGGG CTTCATGAAA

2601 ATGGGGTGTG CTGCAGTGAT CCTCTTTCTC TCTTGGAGTC TCGAATGGAG

2651 GTGGATGACT ATAGTCAGTA TGAGGAAGAA AGTACAGATG ATTCCTCCTC

2701 TTCTGAGGGC GATGAAGAGG AGGATGACTA TGATGATGAC TTTGAAGACG

2751 ATTTTATTCC TCTTCCTCCA GCTAAGCGCT TGAGGTTAAT AGTTGGAAAA

2801 GACTCTATAG ATATTGACAT TTCTTCAAGG AGAAGAGAAG ATCAGTCTTT

2851 AAGGCTTAAT GCCTAAGCTC TTGGTCTTAA CTTGACCTGG GATAACTACT

FIG. 5B

2901 TTAAAGAAAT AAAAAATTCC AGTCAATTAT TCCTCAACTG AAAGTTTAGT
2951 GGCAGCACTT CTATTGTCCC TTCACTTATC AGCATACTAT TGTAGAAAGT
3001 GTACAGCATA CTGACTCAAT TCTTAAGTCT GATTTGTGCA AATTTTTATC
3051 GTACTTTTTA AATAGCCTTC TTACGTGCAA TTCTGAGTTA GAGGTAAAGC
3101 CCTGTTGTAA AATAAAGGCT CAAGCAAAAT TGTACAGTGA TAGCAACTTT
3151 CCACACAGGA CGTTGAAAAC AGTAATGTGG CTACACAGTT TTTTTAACTG
3201 TAAGAGCATC AGCTGGCTCT TTAATATATG ACTAAACAAT AATTTAAAAC
3251 AAATCATAGT AGCAGCATAT TAAGGGTTTC TAGTATGCTA ATATCACCAG
3301 CAATGATCTT TGGCTTTTTG ATTTATTTGC TAGATGTTTC CCCCTTGGAG
3351 TTTTGTCAGT TTCACACTGT TTGCTGGCCC AGGTGTACTG TTTGTGGCCT
3401 TTGTTAATAT CCCAAACCAT TGGTTGGGAG TCAGATTGGT TTCTTAAAAA
3451 AAAAAAAAAA ATGACATACG TGACAGCTCA CTTTTCAGTT CATTATATGT
3501 ACGAGGGTAG CAGTGTGTGG GATGAGGTTC GATACAGCGT ATTTATTGCT
3551 TGTCATGTAA ATTAAAAACC TTGTATTTAA CTCTTTTCAA TCCTTTTAGA
3601 TAAAATTGTT CTTTGCAAGA ATGATTGGTG CTTATTTTTT CAAAAATTTG
3651 CTGTGAACAA CGTGATGACA ACAAGCAACA TTTATCTAAT GAACTACAGC
3701 TATCTTAATT TGGTTCTTCA AGTTTCTGT TGCACTTGTA AAATGCTACA
3751 AGGAATATTA AAAAAATCTA TTCACTTTAA CTTATAATAG TTTATGAAAT
3801 AAAAACATGA GTCACAGCTT TGTTCTGTG GTAACCTATA AAAAAGTTT
3851 GTCTTTGAGA TTCAATGTAA AGAACTGAAA ACAATGTATA TGTTGTAAAT
3901 ATTTGTGTGT TGTGAGACAT TTTTGTCATA AGAAATTAAA AGAACTTACC
3951 AGGAAGGTTT TTAAGTTTAG AAATATTCAT GCCAATAAAA TAGGAAATTA
4001 TAAATATATA GTTTTAAGCA CTGCATCAGT GGGAGTTCTT GGCTTATGTT
4051 AGTTTATGTT AGTTTATTAT GAAAACATCA AAGATTTTTT TGACTATATT
4101 ATCAGTTAAA CAAAAGGAG TCAGATTTAA TTTGTTTTTT GAAGCACTTT
4151 GAGAAATTAA TTTTAATTAA CTTAATGAGC AAATTTTTAT TACTACTTTA
4201 TGTTCAATAC CAGGTTCTTT TCATTTCTCT GGATTATTTT GCAAATCATT
4251 GGACAGAGAA TTTGGGAATA TAAATCTGTA ACAGGTGTTG ACACCAGTAG
4301 GTCTCTTTAT TTCTGGGAAA TGTGTACCTG TACTTTCTGA TATACAGTGT

FIG. 5C

```
4351  TCCTAAGTAA AAATCAATTC AGGGGATTTG TATAGTGTCT ATAGGAAAGT
4401  AGCCCATGTC TTGAAATATG AAAAGGAATC TGAAGGTCAT GAAAAGTCCA
4451  GTGGAGAAAA TCTCAATGCT TACTGTTACT ACTAATTGAT TCCTACTAGT
4501  TTCCAGGTTT GGGGGGATAT TGTTTCAATG ACGCTCCTTA AGACTGTTGA
4551  TTGCCCATAG GTTCCAAATA GAAATTAAGA CTCATGAACA TTTTTAGAAA
4601  GTAGATTGTT TTCTCCTGGT TCTCTAAGGA ACTACTTCTG CAGTCTTACA
4651  TAGTCTCATC CTTGTTTGTT GTGGTGCAGT CGAACTCCTC AGGCGTTTGG
4701  AAAGCATGTG GTAGACCTTC TTCCACACCC ACCCATACCC CCGTTCACTG
4751  CGTCTGGAGG TCTTCAACAG TGAAGTAGGG CAGCCCACAC AGCCTCTCAG
4801  GAGCACCTGT CCGAGGCACC CGGAGCACTT TGCAGAGCAC GTCCAGCCCT
4851  CATGGGGTCC CTGCATAGAA ATGTGAACCC CTGCCACTGA GGAAGATGAA
4901  GGTAGACCCT GTGTCTGGAG GTGCTGGAGG GCAGCGGGTC ACCTCTTGTA
4951  TTCCCACCTT AGTTTGGGGT GTTTTGAAGA GGTTCAGAGA CTAAATCTTA
5001  AACCTTATTT GAATACCAAC GATAGCTATT TTGGGAATTT CGATCTTAAA
5051  AAGTGACAAA ACACATTTCC CATTTTCATT TTTCAGCTGA ATTTTAGTAA
5101  CTTATTTTTG ATGTTTTAAT TTTATCATGG CCTCCTCTTT GGAGGCCAAC
5151  CTTCCCATGG GTCTCAAAGC AGTGACATTT GGTAGTAAAT CACTGCCTCT
5201  CAGGAGTCGG TATGCACAAG CACTCAGCAG CCACTGTTGA TGCCTTCTAG
5251  GGAAACCTAA TTTCCGTTGG TAAAGGTAGG GGCCTCGGAA CTGTTCCGGA
5301  TCTGCTGTAG AACTTCACCG TGTGGAATGG TGACAGCCAC ACACCGTTGA
5351  CCAGTTTAGA AGAGGTTGCA TTCAATAAAA CTCTTAGCTT GAGCTTATGC
5401  AATGATTGGT TAAGATTTTG GCATTGTAAG AATTAGGAGA TGATCATAGA
5451  AATATATGTA AAGTATTCAA TTTTCAATCA TTTTCAAATT ACTGTTATAA
5501  ATTGTTTTTG CTGAGTTGTA ATACTTTTGA GATACAATGT ATTCCTTGTA
5551  CTGAAAGAAT GAAAAAGGAC TTTTTCAGCA TTTGAGGTAA GTTCTTTAAC
5601  GTTTCATTAA AAACATTTTT TACAAATATT TTGTACATGC ACTTGCAGTA
5651  TTGAGGTTAA TCATTTTAAT AAATTCGGAA ATTAAAAAAA
```

(SEQ ID NO:13)

FIG. 5D

```
  1  MVVNGRRNGG KLSNDHQQNQ SKLQHTGKDT LKAGKNAVER RSNRCNGNSG
 51  FEGQSRYVPS SGMSAKELCE NDDLATSLVL DPYLGFQTHK MNTSAFPSRS
101  SRHFSKSDSF SHNNPVRFRP IKGRQEELKE VIERFKKDEH LEKAFKCLTS
151  GEWARHYFLN KNKMQEKLFK EHVFIYLRMF ATDSGFEILP CNRYSSEQNG
201  AKIVATKEWK RNDKIELLVG CIAELSEIEE NMLLRHGEND FSVMYSTRKN
251  CAQLWLGPAA FINHDCRPNC KFVSTGRDTA CVKALRDIEP GEEISCYYGD
301  GFFGENNEFC ECYTCERRGT GAFKSRVGLP APAPVINSKY GLRETDKRLN
351  RLKKLGDSSK NSDSQSVSSN TDADTTQEKN NATSNRKSSV GVKKNSKSRT
401  LTRQSMSRIP ASSNSTSSKL THINNSRVPK KLKKPAKPLL SKIKLRNHCK
451  RLEQKNASRK LEMGNLVLKE PKVVLYKNLP IKKDKEPEGP AQAAVASGCL
501  TRHAAREHRQ NPVRGAHSQG ESSPCTYITR RSVRTRTNLK EASDIKLEPN
551  TLNGYKSSVT EPCPDSGEQL QPAPVLQEEE LAHETAQKGE AKCHKSDTGM
601  SKKKSRQGKL VKQFAKIEES TPVHDSPGKD DAVPDLMGPH SDQGEHSGTV
651  GVPVSYTDCA PSPVGCSVVT SDSFKTKDSF RTAKSKKKRR ITRYDAQLIL
701  ENNSGIPKLT LRRRHDSSSK TNDQENDGMN SSKISIKLSK DHDNDNNLYV
751  AKLNNGFNSG SGSSSTKLKI QLKRDEENRG SYTEGLHENG VCCSDPLSLL
801  ESRMEVDDYS QYEEESTDDS SSSEGDEEED DYDDDFEDDF IPLPPAKRLR
851  LIVGKDSIDI DISSRRREDQ SLRLNA*
```

(SEQ ID NO:14)

FIG. 6

```
185                       GFEILP CNRYSSEQNG

201  AKIVATKEWK RNDKIELLVG CIAELSEIEE NMLLRHGEND FSVMYSTRKN

251  CAQLWLGPAA FINHDCRPNC KFVSTGRDTA CVKALRDIEP GEEISCYYGD

301  GFFG
```

(SEQ ID NO:14)

FIG. 7

APOPTIN-ASSOCIATING PROTEIN

CROSS-REFERENCE TO RELATED APPLICATION

This application is a divisional of U.S. patent application Ser. No. 09/733,416, filed Dec. 8, 2000, now U.S. Pat. No. 7,256,274, issued Aug., 14, 2007, which itself claims priority from European Patent Office application 00250119.5 filed Apr. 7, 2000, and European Patent Office application 99204242.4 filed Dec. 10, 1999, the contents of the entirety of each of which are incorporated by this reference.

TECHNICAL FIELD

The invention relates generally to biotechnology, and, more particularly, to the field of apoptosis.

BACKGROUND

Apoptosis is an active and programmed physiological process for eliminating superfluous, altered or malignant cells (Earnshaw, 1995; Duke et al., 1996). Apoptosis is characterized by shrinkage of cells, segmentation of the nucleus, condensation and cleavage of DNA into domain-sized fragments, in most cells followed by internucleosomal degradation. The apoptotic cells fragment into membrane-enclosed apoptotic bodies. Finally, neighboring cells and/or macrophages will rapidly phagocytose these dying cells (Wyllie et al., 1980; White, 1996). Cells grown under tissue-culture conditions and cells from tissue material can be analyzed for being apoptotic with agents staining DNA, as, e.g., DAPI, which stains normal DNA strongly and regularly, whereas apoptotic DNA is stained weakly and/or irregularly (Noteborn et al., 1994; Telford et al., 1992).

The apoptotic process can be initiated by a variety of regulatory stimuli (Wyllie, 1995; White, 1996; Levine, 1997). Changes in the cell survival rate play an important role in human pathogenesis of diseases, e.g., in cancer development and auto-immune diseases, where enhanced proliferation or decreased cell death (Kerr et al., 1994; Paulovich, 1997) is observed. A variety of chemotherapeutic compounds and radiation have been demonstrated to induce apoptosis in tumor cells, in many instances via wild-type p53 protein (Thompson, 1995; Bellamy et al., 1995; Steller, 1995; McDonell et al., 1995).

Many tumors, however, acquire a mutation in p53 during their development, often correlating with poor response to cancer therapy. Certain transforming genes of tumorigenic DNA viruses can inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-abl is associated with a strong resistance to various apoptosis-inducing chemotherapeutic agents (Hockenberry 1994; Sachs and Lotem, 1997).

For such tumors lacking functional p53 (representing more than half of the tumors), alternative anti-tumor therapies are under development based on induction of apoptosis independent of p53 (Thompson 1995; Paulovich et al., 1997). One has to search for the factors involved in induction of apoptosis, which do not need p53 and/or cannot be blocked by anti-apoptotic activities, such as Bcl-2 or Bcr-abl-like ones. These factors might be part of a distinct apoptosis pathway or might be (far) downstream of the apoptosis-inhibiting compounds.

Apoptin is a small protein derived from chicken anemia virus (CAV; Noteborn and De Boer, 1995; Noteborn et al., 1991; Noteborn et al., 1994; 1998a), which can induce apoptosis in human malignant and transformed cell lines, but not in untransformed human cell cultures. In vitro, Apoptin fails to induce programmed cell death in normal lymphoid, dermal, epidermal, endothelial and smooth-muscle cells. However, when normal cells are transformed, they become susceptible to apoptosis by Apoptin. Long-term expression of Apoptin in normal human fibroblasts revealed that Apoptin has no toxic or transforming activity in these cells (Danen-van Oorschot, 1997; and Noteborn, 1996).

In normal cells, Apoptin was found predominantly in the cytoplasm, whereas in transformed or malignant cells, i.e., characterized by hyperplasia, metaplasia or dysplasia, it was located in the nucleus, suggesting that the localization of Apoptin is related to its activity (Danen-van Oorschot et al. 1997).

Apoptin-induced apoptosis occurs in the absence of functional p53 (Zhuang et al., 1995a), and cannot be blocked by Bcl-2, Bcr-abl (Zhuang et al., 1995), or the Bcl-2-associating protein BAG-1 (Danen-Van Oorschot, 1997a; Noteborn, 1996).

Therefore, Apoptin is a therapeutic compound for the selective destruction of tumor cells, or other hyperplasia, metaplasia or dysplasia, especially for those tumor cells that have become resistant to (chemo)-therapeutic induction of apoptosis, due to the lack of functional p53 and (over)-expression of Bcl-2 and other apoptosis-inhibiting agents (Noteborn and Pietersen, 1998). It appears that even pre-malignant, minimally transformed cells, are sensitive to the death-inducing effect of Apoptin. In addition, Noteborn and Zhang (1998) have shown that Apoptin-induced apoptosis can be used as diagnosis of cancer-prone cells and treatment of cancer-prone cells.

The fact that Apoptin does not induce apoptosis in normal human cells, at least not in vitro, shows that a toxic effect of Apoptin treatment in vivo will be very low. Noteborn and Pietersen (1998) and Pietersen et al. (1999) have provided evidence that adenovirus-expressed Apoptin does not have an acute toxic effect in vivo. In addition, in nude mice it was shown that Apoptin has a strong anti-tumor activity.

However, to further enlarge the array of therapeutic anti-cancer or anti-auto-immune-disease compounds available in the art, additional therapeutic compounds are desired that are designed to work alone, sequentially to, or jointly with Apoptin, especially in those cases wherein p53 is (partly) non-functional.

The invention provides, for example, novel combinatorial therapies or novel therapeutic compounds that can work alone, sequentially to, or jointly with Apoptin, especially in those cases wherein p53 is non-functional or partially non-functional.

BRIEF DESCRIPTION OF THE DRAWINGS

FIG. 1 shows the partial sequence (SEQ ID NO:10) of vector pMT2SM-AAP-4. The DNA sequence of the AAP-4 cDNA starts at position 12 of the DNA sequence and is indicated as "start AAP4 cDNA."

FIG. 2 shows the amino acid sequence (SEQ ID NO:12) of the analyzed region of the Apoptin-associating clone AAP-4 (bold). In addition, the three C-terminal amino acids H-E-G of the multiple cloning site of pACT are given to illustrate that the AAP-4 amino acid sequence is in frame with the GAL4-activation domain. This feature proves that the AAP-4 region is indeed synthesized in yeast cells.

FIG. 3 shows the apoptotic activity of AAP-4 protein and/or Apoptin in human osteosarcoma-derived Saos-2 cells and in human osteosarcoma U2OS cells. (−): no apoptotic activity; (++): strong apoptotic activity; (+++): very strong apoptotic activity. In total, three independent experiments have been carried out for both cell types.

FIG. 5 shows the nucleic acid sequence (SEQ ID NO:13) of full-length AAP-4.

FIG. 6 shows the amino acid sequence (SEQ ID NO:14) deduced from the nucleic acid sequence of FIG. 5.

FIG. 7 shows the SET domain (SEQ ID NO:14) of the AAP-4 protein.

DESCRIPTION OF THE PREFERRED EMBODIMENTS

Figure 4:
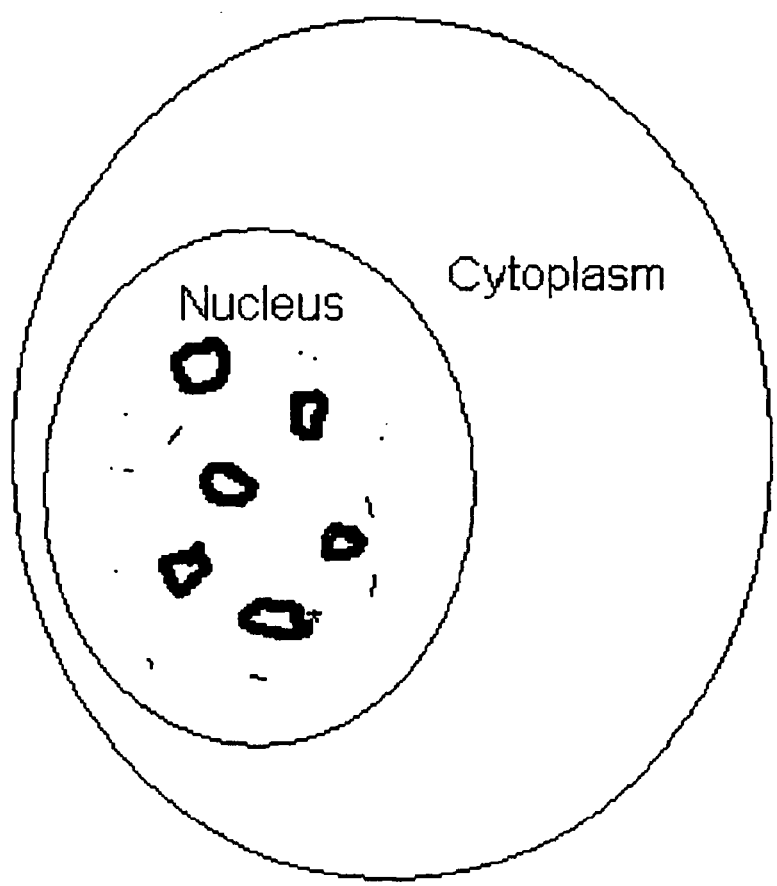
FIG. 4 shows a schematic representation of the nuclear "circular" apoptotic structures containing AAP-4 protein, which are visible in human tumor cells undergoing apoptosis.

In certain embodiments, provided is an isolated or recombinant nucleic acid or functional equivalent or fragment thereof encoding an Apoptin-associating proteinaceous substance capable of nuclear localization, or nuclear co-localization with Apoptin, and is capable of providing apoptosis, alone or in combination with other apoptosis-inducing substances, such as Apoptin, particularly in transformed cells or tumor cells. In certain embodiments, it co-localizes with chromatin/DNA structures in the nucleus of the cell, in an initial apoptotic phase leading up to segmentation of the nucleus, condensation and cleavage of DNA into fragments, in most of the cells followed by internucleosomal degradation. In another embodiment of the invention, the substance allows co-localization that takes place in a somewhat organized pattern whereby circular structures are formed in the nucleus, particularly in an area of the nucleus containing heterochromatin. However, during the above-described apoptotic segmentation of the nucleus by condensation and cleavage of DNA into fragments, the euchromatin is, of course, also affected.

"Proteinaceous substance" is defined herein as a substance comprising a peptide, polypeptide or protein, optionally having been modified by, for example, glycosylation, myristilation, phosphorylation, the addition of lipids, by homologous or heterologous di- or multimerization, or any other (post-translational) modifications known in the art.

"Apoptin-associating" is defined herein as belonging to the cascade of substances specifically involved in the cascade of events found in the apoptosis pathway as inducible by Apoptin, preferably those substances that are specifically involved in the p53-independent apoptosis pathway.

In certain embodiments, the invention provides an isolated or recombinant nucleic acid or functional equivalent or fragment thereof encoding an Apoptin-associating proteinaceous substance capable of providing apoptosis derived from a cDNA library, preferably a vertebrate cDNA library, such as derivable from poultry, but more preferably a mammalian cDNA library, preferably wherein the cDNA library comprises human cDNA. An Apoptin-associating proteinaceous substance obtained by determining a vertebrate analogue (preferably human) of an Apoptin-associating proteinaceous substance derived from an invertebrate cDNA library is also included.

In certain other embodiments, the invention provides an isolated or recombinant nucleic acid or functional equivalent or fragment thereof encoding an Apoptin-associating proteinaceous substance capable of providing apoptosis capable of hybridizing to a nucleic acid molecule encoding an Apoptin-associating proteinaceous substance capable of providing apoptosis as shown in FIG. 1 or FIG. 5, in particular encoding a novel protein capable of providing apoptosis or a functional equivalent or functional fragment thereof called Apoptin-associating protein 4, abbreviated herein also as AAP-4. FIG. 1 shows an approximately 750 bp fragment of the complete AAP-4 fragment as depicted in FIG. 5. Both nucleotide sequences encode a protein with at least the capability of binding to Apoptin and providing apoptosis. Of course, an isolated or recombinant nucleic acid or functional equivalent or fragment thereof encoding an additional Apoptin-associating proteinaceous substance capable of associating with the partial or complete AAP-4 protein are herewith also provided, means and methods to arrive at such an additional protein located in the Apoptin cascade follow in the detailed description given herein. Knowledge derived from studying the partial- or full-length AAP-4 is exploited to determine a functional pathway in which partial- or full-length AAP-4 is involved, thus allowing the design of a therapeutic means of intervention in such a pathway.

In particular, the invention provides an isolated or recombinant nucleic acid or functional equivalent or fragment thereof encoding an Apoptin-associating proteinaceous substance capable of providing apoptosis being at least 60% homologous, preferably at least 70%, more preferably at least 80%, even more preferably 90% and most preferably at least 95%, homologous to a nucleic acid molecule, or to a functional equivalent or functional fragment thereof, encoding an Apoptin-associating proteinaceous substance as shown in FIG. 1 or FIG. 5.

Furthermore, the invention provides a vector comprising a nucleic acid according to the invention. Examples of such a vector are given in the detailed description given herein; such as vector pMT2SM-AAP-4, pMT2SM vector expressing Myc-tagged AAP-4 cDNA, a plasmid expressing an Apoptin-associating protein fragment, and so on. These and other vectors are, for example, useful in finding additional Apoptin-associating proteinaceous substances from the cascade, as defined above.

In yet another embodiment, the invention provides a vector comprising a nucleic acid according to the invention, the vector comprising a gene-delivery vehicle, making the invention very useful in gene therapy. By equipping a gene delivery vehicle with a nucleic acid according to the invention, and by targeting the vehicle to a cell or cells that have been over-proliferating and/or have shown decreased death rates, the gene delivery vehicle provides the cell or cells with the necessary means for apoptosis, providing far-reaching therapeutic possibilities.

Furthermore, provided is a host cell comprising a nucleic acid or a vector according to the invention. Examples comprise transformed or transfected bacterial or yeast cells as described in the detailed description herein. Preferred is a host cell according to the invention that is a transformed eukaryotic cell such as a yeast cell or a vertebrate cell, such as mammalian or Cos cells transformed or transfected with a nucleic acid or vector according to the invention. The cells are, in general, capable of expressing or producing a proteinaceous substance capable of providing apoptosis with the ability to associate with Apoptin.

Furthermore provided is an isolated or recombinant Apoptin-associating proteinaceous substance capable of providing apoptosis. As, for example, shown herein in FIG. 3, expression of such Apoptin-associating proteinaceous substance in cells, such as tumor cells or other over-proliferating cells, induces the apoptotic process. It can do so alone or in the presence of other apoptosis-inducing substances such as Apoptin, and especially so independent of p53, showing that also in those cases where (functional) p53 is absent, apoptosis can be induced by a substance according to the invention. In particular, the invention provides a proteinaceous substance according to the invention encoded by a nucleic acid according to the invention, for example, comprising at least a part of an amino acid sequence as shown in FIG. 2 or FIG. 6 or a functional equivalent or functional fragment thereof capable of providing apoptosis alone or in combination, preferably co-localizing, with other apoptosis-inducing substances such as Apoptin (see, for example, FIG. 4, where circular structures are shown where Apoptin and a substance as provided were found to co-localize in transformed or tumor cells).

Also provided is an isolated or synthetic antibody specifically recognizing a proteinaceous substance or functional equivalent or functional fragment thereof according to the invention. Such an antibody is, for example, obtainable by immunizing an experimental animal with an Apoptin-associating proteinaceous substance or an immunogenic fragment or equivalent thereof and harvesting polyclonal antibodies from the immunized animal (as shown herein in the detailed description), or obtainable by other methods known in the art such as by producing monoclonal antibodies, or (single chain) antibodies or binding proteins expressed from recombinant nucleic acid derived from a nucleic acid library, for example, obtainable via phage display techniques.

With such an antibody, the invention also provides a proteinaceous substance specifically recognizable by such an antibody according to the invention, for example, obtainable via immunoprecipitation, Western Blotting, or other immunological techniques known in the art.

Furthermore, provided is the use of a nucleic acid, vector, host cell, or proteinaceous substance according to the invention for the induction of apoptosis, as, for example, shown in FIG. 3. In particular, such use is provided wherein apoptosis is p53-independent. In particular, such use is also provided further comprising use of a nucleic acid encoding Apoptin or a functional equivalent or fragment thereof or use of Apoptin or a functional equivalent or fragment thereof. As can be seen from FIG. 3, combining these Apoptin-inducing substances increases the percentage apoptosis of treated tumor cells.

Such use as provided by the invention is particularly useful from a therapeutic viewpoint. The invention provides herewith a pharmaceutical composition comprising a nucleic acid, vector, host cell, or proteinaceous substance according to the invention. In addition, such a pharmaceutical composition according to the invention is provided further comprising a nucleic acid encoding Apoptin or a functional equivalent or fragment thereof or Apoptin or a functional equivalent or fragment thereof.

Such a pharmaceutical composition is, in particular, provided for the induction of apoptosis, for example, wherein apoptosis is p53-independent, for the treatment of a disease where enhanced cell proliferation or decreased cell death is observed, as is in general the case when the disease comprises cancer or auto-immune disease. Herewith, provided is a method for treating an individual carrying a disease where enhanced cell proliferation or decreased cell death is observed comprising treating the individual with a pharmaceutical composition according to the invention. In particular, these compositions comprise a factor of an apoptosis pathway, which is specific for transformed cells and cancer-prone cells. Therefore, these compositions are not only essential for new treatments, but also for diagnosis of diseases related with aberrances in the apoptotic process, such as cancer and auto-immune diseases.

Furthermore, the invention provides for diagnosis of cancer-prone cells in particular by detecting those cells that under influence of a substance (e.g., by transfection) as provided by the invention, show condensing of chromatin/DNA or circular structures as described in FIG. 4.

The invention also provides an isolated or recombinant nucleic acid encoding a proteinaceous substance comprising the amino acid sequence as shown in FIG. 7.

In a further embodiment, the invention provides an assay to identify a putative effector of the activity of the proteinaceous substance encoded by a nucleic acid as shown in FIG. 5 comprising bringing in contact a proteinaceous substance comprising amino acid 852-900 of the amino acid sequence shown in FIG. 6 with the effector and determining the binding of the effector.

The following examples are offered by way of illustration of the present invention, not limitation.

EXPERIMENTAL

The yeast-2 hybrid system (Durfee et al., 1993) was used to identify Apoptin-associating cellular compounds, which are essential in the induction of apoptosis. The system used is an in vivo strategy to identify human proteins capable of physically associating with Apoptin. It has been used to screen cDNA libraries for clones encoding proteins capable of binding to a protein of interest (Fields and Song, 1989; Yang et al., 1992). Provided is, for example, a novel Apoptin-associating protein, one of which is named Apoptin-associating protein 4 abbreviated as AAP-4. The invention also provides a method for inducing apoptosis through interference with the function of this newly discovered AAP-4 protein or functional equivalents or fragments thereof and/or the induction of apoptosis by means of expression or overexpression ("(over)expression") of AAP-4 or related gene or functional equivalents or fragments thereof.

The invention also provides an anti-tumor therapy based on the interference with the function of AAP-4-like proteins and/or its (over)expression. An aberrantly high level of AAP-4-like proteins will result in the induction of the opposite process of cell transformation, namely apoptosis. The invention furthermore provides the mediator of Apoptin-induced apoptosis, which is tumor-specific. The invention provides a therapy for cancer, auto-immune diseases or related diseases that is based on AAP-4-like proteins alone or in combination with Apoptin and/or Apoptin-like compounds.

Construction of pGBT9-VP3

For the construction of the bait plasmid, which enables the identification of Apoptin-associating proteins by means of a yeast-2 hybrid system, plasmid pET-16b-VP3 (Notebom, unpublished results) was treated with NdeI and BamHI. The 0.4 kb NdeI-BamHI DNA fragment was isolated from low-melting-point agarose. Plasmid pGBT9 (Clontech Laboratories, Inc., Palo Alto, US) was treated with the restriction enzymes EcoRI and BamHI. The about 5.4-kb DNA fragment was isolated and ligated to an EcoRI-NdeI linker and the 0.4-kb DNA fragment containing the Apoptin-encoding sequences starting from its own ATG-initiation codon. The final construct containing a fusion gene of the GAL4-binding domain sequence and Apoptin under the regulation of the yeast promoter ADH was called pGBT-VP3 and was proven to be correct by restriction-enzyme analysis and DNA-sequencing according to the Sanger method (1977).

All cloning steps were essentially carried out as described by Maniatis et al. (1992). The plasmid pGBT-VP3 was purified by centrifugation in a CsCl gradient and column chromatography in Sephacryl S500 (Pharmacia).

GAL4-Activation Domain-Tagged cDNA Library

The expression vector pACT, containing the cDNAs from Epstein-Barr-virus-transformed human B cells fused to the GAL4 transcriptional activation domain, was used for detecting Apoptin-associating proteins. The pACT c-DNA library is derived from the lambda-ACT cDNA library, as described by Durfee et al., 1993.

Bacterial and Yeast Strains

The *E. coli* strain JM109 was the transformation recipient for the plasmid pGBT9 and pGBT-VP3. The bacterial strain electromax/DH10B was used for the transformation needed for the recovery of the Apoptin-associating pACT-cDNAs, and was obtained from GIBCO-BRL, US.

The yeast strain Y190 was used for screening the cDNA library and all other transformations, which are part of the yeast-2 hybrid system used.

Media

For drug selections Luria Broth (LB) plates for *E. coli* were supplemented with ampicillin (50 microgram per ml). Yeast YPD and SC media were prepared as described by Rose et al. (1990).

Transformation of Competent Yeast Strain Y190 with Plasmids pGBT-VP3 and pACT-cDNA and Screening for Beta-Galactosidase Activity The yeast strain Y190 was made competent and transformed according to the methods described by Klebe et al. (1983). The yeast cells were first transformed with pGBT-VP3 and subsequently transformed with pACT-cDNA, and these transformed yeast cells were grown on histidine-minus plates, also lacking leueine and tryptophan.

Hybond-N filters were placed on yeast colonies, which were histidine-positive and allowed to wet completely. The filters were lifted and submerged in liquid nitrogen to permeabilize the yeast cells. The filters were thawed and laid with the colony side up on Whattman 3 mM paper in a petri dish with Z-buffer (per liter: 16.1 gr $Na_2HPO_4.7H_2O$, 5.5 gr $NaH_2PO_4.H_2O$, 0.75 gr KCl and 0.246 gr $MgSO_4.7H_2O$, pH 7.0) containing 0.27% beta-mercapto-ethanol and 1 mg/ml X-gal. The filters were incubated for at least 15 minutes or during the night.

Recovery of Plasmids from Yeast

Total DNA from yeast cells, which were histidine- and beta-galactosidase-positive, was prepared by using the glusulase-alkaline lysis method as described by Hoffman and Winston (1987) and used to transform Electromax/DH10B bacteria via electroporation using a Bio-Rad GenePulser according the manufacturer's specifications.

Transformants were plated on LB media containing the antibiotic agent ampicillin.

Isolation of Apoptin-Associating pACT Clones

By means of colony-filter assay, the colonies were lysed and hybridized to a radioactive-labeled 17-mer oligomer, which is specific for pACT (see also, section Sequence analysis). Plasmid DNA was isolated from the pACT clones, and by means of XhoI digestion analyzed for the presence of a cDNA insert.

Sequence Analysis

The subclone containing the sequence encoding Apoptin-associating protein was partially sequenced using dideoxy NTPs according to the Sanger-method, which was performed by Eurogentec, Seraing, Belgium. The used sequencing primer was a pACT-specific 17-mer comprising of the DNA-sequence 5'-TACCACTACAATGGATG-3' (SEQ ID NO:1 of the herein incorporated SEQUENCE LISTING).

The sequences of the Apoptin-associating cDNAs were compared with known gene sequences from the EMBL/Genbank.

Generation and Testing of Antibodies

In order to generate polyclonal antisera against the AAP-4 protein, we designed three peptides. These peptides were:

1) EESTPVHDSPGKDDA (SEQ ID NO:2)

2) DSFKTKDSFRTAKSK (SEQ ID NO:3)

3) IDIDISSRRREDQSL (SEQ ID NO:4)

These peptides were synthesized at Eurogentec (Belgium) with the standard addition of a C-terminal cysteine residue and all subsequent antibody syntheses was also performed there. These peptides were coupled to Keyhole Limpet Hemocyanin (KLH) and injected as a cocktail into two separate specific pathogen-free rabbits with an immunization schedule of one injection and three subsequent boosts. Blood samples were taken before and after immunization. The sera were tested in-house for specific reactivity to the peptide cocktail by ELISA. The titers from each rabbit were high (>200,000). Furthermore, for certain subsequent purposes, the AAP-4 antibody was immune-purified using peptide cocktail coupled to immobilized diaminodipropylamine agarose columns (Pierce) according to the manufacturer's protocol.

The best AAP-4 antibody preparation of the two generated was selected for further use. We tested the efficacy of this antibody by transfecting 6 cm plates of sub-confluent primate COS-7 and human U2OS cells using the calcium phosphate co-precipitation method with 5 ug of the AAP-4-myc construct, and as a control, untransfected cells. Two days post-transfection, cells were washed briefly in PBS, lysed in RIPA buffer (10 mM Tris 7.5, 150 mM NaCl, 0.1% SDS, 1.0% NP-49 and 1.0% sodium deoxycholate), clarified by centrifugation, and the supernatant fractionated on SDS-denaturing polyacrylamide gel electrophoresis. Proteins were Western-transferred to PVDF membranes (Immobilon, Millipore) using standard methodology. Membranes were blocked in 5% non-fat dry milk in tris-buffered saline containing 0.1% Tween-20, then incubated in the unpurified AAP-4 antisera at a concentration of 1:5000. After a brief wash, membranes were further incubated in HRP-conjugated goat-anti-rabbit Ig at a concentration of 1:2000. After a thorough series of wash steps, proteins were detected using enhanced chemiluminescence (Amersham) according to the manufacturer's protocol, and exposed to x-ray film and developed using standard automated machinery.

In addition, we tested the purified AAP-4 antibody using immunoprecipitation in a manner the same as above, except that after centrifugation, the supernatant was added to 10 μl of AAP-4 antibody pre-coupled to protein-A-sepharose beads, incubated for one hour with tumbling, then washed before fractionation on SDS-PAGE gels and Western analysis. Detection in this case was performed with the anti-myc tag monoclonal antibody 9E10 (Evan et al., 1985).

Finally, the purified antibody was tested for utility in immunofluorescence by including glass coverslips in the above transfections. Coverslips were fixed with 4% paraformaldehyde, blocked with normal goat serum, incubated in AAP-4 antibody diluted 1:5, washed, incubated in FITC-conjugated goat-anti-rabbit Ig, mounted and visualized under fluorescence microscopy.

Northern Blot Analysis

To examine whether AAP-4 was differentially expressed in tumor versus normal tissue, we tested a commercially available Northern blot (Invitrogen, cat. No. #D310001) that contained tumor and normal tissue derived from the same patient, from a variety of tissue types. The DNA probe was derived from an internal HindIII fragment of AAP-4 and was labeled with $^{32}$P-dATP using the MegaPrime kit of Amersham. All prehybridization, hybridization and washing steps were done according to the Northern blot manufacturer's recommendation. Further guidance for hybridization conditions is provided in *Molecular Cloning, A Laboratory Manual*, by Sambrook, et al. (1989), published by Cold Spring Harbor Laboratory Press. Blots were subjected to autoradiography and developed using standard automated methods.

Cloning of Full-Length AAP-4

A human brain cDNA library was obtained from Clontech (Marathon-Ready™ cDNA). The cDNA for AAP-4 was generated in a RACE-PCR (Rapid Amplification of cDNA Ends) according to the manufacturer's instructions included in the Marathon-Ready™ cDNA kit. For the RACE-PCR, the following "touch-down" program was used in a Perkin-Elmer 9600 thermocycler: one cycle 94° C. 30 seconds; five cycles of 94° C. five seconds, 72° C. three minutes; five cycles of 94° C. five seconds, 70° C. three minutes; 25 cycles of 94° C. five seconds, 68° C. three minutes. The sequences of the AAP-4 primers used in the RACE reaction were:

```
AAP-4#3F
                                      (SEQ ID NO:5)
5' GTC AGC TCT AAC ACT GAT GCA GAT ACC AC 3'

AAP-4#3R
                                      (SEQ ID NO:6)
5' GTG GTA TCT GCA TCA GTG TTA GAG CTG AC 3'
```

The RACE products were cloned in the pCR®4-TOPO vector according to the instructions of the TOPO-TA cloning kit from Invitrogen. The sequences of the cloned PCR products were amplified with the Applied Biosystem (ABI) Prism®BigDye™ Terminator sequencing kit and analyzed in the ABI 310 capillary sequencer. The complete open reading frame (ORE) of AAP-4 was subsequently amplified in the following PCR reaction: one cycle 94° C. 30 seconds; 30 cycles 94° C. five seconds, 68° C. three minutes. The gene-specific primers had the following sequences:

```
AAP-4#8F
                                      (SEQ ID NO:7)
5' GAG AGT GAC TAA ATG CAC CTG GGT CAG G 3'

AAP-4#9R
                                      (SEQ ID NO:8)
5' GTT ATC CCA GGT CAA GTT AAG ACC 3'
```

The full-length generated product cloned into the pCR®4-TOPO vector was subjected to a final sequence analysis as previously described.

Results and Discussion

Apoptin induces apoptosis specifically in transformed cells, such as cell lines derived from human tumors. To identify the essential compounds in this cell-transformation-specific and/or tumor-specific apoptosis pathway, a yeast genetic screen was carried out.

We have used a human cDNA library, which is based on the plasmid vector pACT containing the complete cDNA copies made from Epstein-Barr virus-transformed human B cells (Durfee et al., 1993).

Construction of a Bait Plasmid Expressing a Fusion Gene Product of GAL4-DNA-Binding Domain and Apoptin To examine the existence of Apoptin-associating proteins in the human transformed/tumorigenic cDNA library, a so-called bait plasmid had to be constructed. To that end, the complete Apoptin-encoding region, flanked by about 40 basepairs downstream from the Apoptin gene, was cloned in the multiple cloning site of plasmid pGBT9.

The final construct, called pGBT-VP3, was analyzed by restriction-enzyme analysis and sequencing of the fusion area between Apoptin and the GAL4-DNA-binding domain.

A Gene (Fragment) Encoding an Apoptin-Associating Protein is Determined by Transactivation of a GAL4-Responsive Promoter in Yeast The Apoptin gene was fused to the GAL4-DNA-binding domain of plasmid pGBT-VP3, whereas all cDNAs derived from the transformed human B cells are fused to the GAL4-activation domain of plasmid pACT. If one of the proteinaceous substances encoded by the cDNAs binds to Apoptin, the GALA-DNA-binding domain would be in the vicinity of the GAL4-activation domain resulting in the activation of the GAL4-responsive promoter, which regulates the reporter genes HIS3 and LacZ.

The yeast clones containing plasmid-expressing Apoptin and a plasmid expressing an Apoptin-associating protein fragment can grow on a histidine-minus medium and will stain blue in a beta-galactosidase assay. Subsequently, the plasmid with the cDNA insert encoding the Apoptin-associating protein can be isolated and characterized.

Before we did so, however, we determined that transformation of yeast cells with pGBT-VP3 plasmid alone, or in combination with an empty pACT vector, did not result in the activation of the GAL4-responsive promoter.

Identification of Apoptin-Associating Protein Encoded by cDNA Derived from a Human Transformed B Cell Line We have found one yeast colony that, upon transformation with pGBT-VP3 and pACT-cDNA, was able to grow on a histidine-minus medium (also lacking leucine and tryptophan) and stained blue in a beta-galactosidase assay. These results indicate that the observed yeast colony also contained, besides the bait plasmid pGBT-VP3, a pACT plasmid encoding a potential Apoptin-associating protein.

Plasmid DNA was isolated from the positive yeast colony and transformed in bacteria. By means of a filter-hybridization assay using a pACT-specific labeled DNA-probe, the clone containing pACT plasmid could be determined.

Subsequently, pACT DNA was isolated and digested with restriction enzyme XhoI, which resulted in the presence of a 2.1-kbp cDNA insert. Finally, the insert of pACT plasmid containing the cDNA insert was fully sequenced by using the Sanger method (Sanger et al., 1977).

Description of Apoptin-Associating Proteins

The yeast genetic screen for Apoptin-associating proteins resulted in the detection of a cDNA clone comprising a single type of protein, namely a novel protein called Apoptin-associating protein 4, abbreviated as AAP-4.

The determined DNA sequence part of the AAP-4 cDNA clone is shown in FIG. 1. The amino acid sequence derived from the detected DNA sequence of clone AAP-4 is given in FIG. 2.

Construction of an Expression Construct for the Identification of AAP-4 Protein in Mammalian Cells To study whether the cloned cDNA AAP-4 indeed encodes (Apoptin-associating) a protein product, we carried out the following experiments.

The DNA plasmid pMT2SM contains the adenovirus 5 major late promoter (MLP) and the SV40 ori enabling high levels of expression of foreign genes in transformed mammalian cells, such as SV-40-transformed Cos cells. Furthermore, the pMT2SM vector contains a Myc-tag (amino acids: EQK-LISEEDL (SEQ ID NO:9)), which is in-frame with the foreign gene product. This Myc-tag enables the recognition of, e.g., Apoptin-associating proteins by means of the Myc-tag-specific 9E10 antibody.

The pMT2SM vector expressing Myc-tagged AAP-4 cDNA was constructed as follows. The pACT-AAP-4 cDNA clone was digested with the restriction enzyme XhoI and the cDNA insert was isolated. The expression vector pMT2SM was digested with XhoI and treated with calf intestine alkaline phosphatase and ligated to the isolated AAP-4 cDNA inserts. By sequence analysis, the pMT2SM constructs containing the AAP-4 cDNA in the correct orientation were identified.

The synthesis of Myc-tagged AAP-4 protein was analyzed by transfection of Cos cells with plasmid pMT2SM-AAP-4. As negative control, Cos cells were mock-transfected. Two days after transfection, the cells were lysed and Western-blot analysis was carried out using the Myc-tag-specific antibody 9E10.

The Cos cells transfected with pMT2SM-AAP-4 were proven to synthesize a specific Myc-tagged AAP-4 product with the size of approximately 60-65 kDa. As expected, the lysates of the mock-transfected Cos cells did not contain a protein product reacting with the Myc-tag-specific antibodies.

These results indicate that we have been able to isolate a cDNA that is able to produce a protein product with the ability to associate to the apoptosis-inducing protein Apoptin.

Co-immunoprecipitation of Myc-Tagged AAP-4 Protein with Apoptin in a Transformed Mammalian Cell System Next, we have analyzed the association of Apoptin and the AAP-4 protein by means of co-immunoprecipitations using the Myc-tag-specific antibody 9E10. The 9E10 antibodies were shown not to bind directly to Apoptin, which enables the use of 9E10 for carrying out co-immuno-precipitations with (myc-tagged) Apoptin-associating proteins and Apoptin.

To that end, Cos cells were co-transfected with plasmid pCMV-VP3-encoding Apoptin and with plasmid pMT2SM-AAP-4. As a negative control, cells were transfected with pCMV-VP3-expressing Apoptin and a plasmid pcDNA3.1.LacZ-myc/His-LacZ encoding the myc-tagged beta-galactosidase, which does not associate with Apoptin.

Two days after transfection, the cells were lysed in a buffer consisting of 50 mM Tris (7.5), 250 mM NaCl, 5 mM EDTA, 0.1% Triton X100, 1 mg/ml $Na_4P_2O_7$ and freshly added protease inhibitors such as PMSF, Trypsin-inhibitor, Leupeptine and $Na_3VO_4$. The specific proteins were immuno-precipitated as described by Noteborn et al. (1998) using the Myc-tag-specific antibodies 9E10, and analyzed by Western blotting.

Staining of the Western blot with 9E10 antibodies and 111.3 antibodies, which are specifically directed against myc-tag and Apoptin, respectively, showed that the "total" cell lysates contained the 16-kDa Apoptin product and the Myc-tagged AAP-4 protein or beta-galactosidase product. Immunoprecipitation of the Myc-tagged AAP-4 products was accompanied by the immuno-precipitation of Apoptin product of 16 kDa. In contrast, immunoprecipitation of myc-tagged beta-galactosidase did not result in a significant co-precipitation of the Apoptin protein. In addition, immunoprecipitation of the Apoptin protein, by means of a polyclonal antibody directed against the C-terminal part of Apoptin (Noteborn and Danen, unpublished results), was accompanied by the immunoprecipitation of the myc-tagged AAP-4 product of 60-65 kDa.

In total, three independent immunoprecipitation experiments were carried out, which all showed the associating ability of Apoptin to the AAP-4 protein.

These results indicate that the novel-determined AAP-4 protein is able to specifically associate with Apoptin, not only in the yeast background, but also in a mammalian transformed cellular system.

Over-Expression of the Novel AAP-4 Protein in Human Osteosarcoma Saos-2 Cells, Lacking Functional p53, Induces the Apoptotic Process We have examined whether AAP-4 carries apoptotic activity in Saos-2 cells. First, we have analyzed the cellular localization of the novel AAP-4 protein in human transformed cells. To that end, the human osteosarcoma-derived Saos-2 cells were transfected, as described by Danen-van Oorschot (1997), with plasmid pMT2SM-AAP-4 encoding the myc-tagged AAP-4 protein, respectively.

By indirect immunofluorescence using the myc-tag-specific antibody 9E10 and DAPI, which stains the nuclear DNA, it was shown that AAP-4 protein was present in the nucleus of the cell. Most often, it co-localizes with the chromatin/DNA structures.

During tumor development, most of the tumors will lack functional tumor suppressor p53. Tumor cells lacking functional p53 are, in general, poor responders to (chemo)therapeutic agents. Therefore, it is of importance to prove whether AAP-4 can induce apoptosis in human tumor cells in the absence of functional p53.

To this end, we examined whether (over-)expression of AAP-4 protein results in induction of apoptosis. Four days after transfection, the majority of AAP-4-positive cells were aberrantly stained with DAPI, which is indicative for induction of apoptosis (Telford, 1992; Danen-van Oorschot, 1997). Cells expressing Apoptin also underwent apoptosis, albeit slightly less than the AAP-4-producing cells, whereas, as expected, the cells synthesizing the non-apoptotic beta-galactosidase (LacZ) protein did not. The results are shown in FIG. 3.

Co-expression of Apoptin and AAP-4 protein in human tumor cells, such as Saos-2 cells, results in a faster apoptotic process than expression of Apoptin or AAP-4 protein alone (FIG. 3).

The fact that AAP-4 protein can induce apoptosis in p53-minus Saos-2 cells indicates that AAP-4 can induce p53-independent apoptosis. These results imply that AAP-4 can be used as anti-tumor agent in cases where other (chemo) therapeutic agents will fail. Furthermore, the finding that both Apoptin and AAP-4 induce a p53-independent pathway indicates that AAP-4 fits in the Apoptin-induced apoptotic pathway.

In conclusion, we have identified an Apoptin-associating protein, namely, the novel AAP-4 protein, which is present in the nucleus and able to induce (p53-independent) apoptosis in human tumor cells.

Over-Expression of the Novel AAP-4 Protein in Human Osteosarcoma U2OS Cells, Expressing Wild-Type p53, Induces the Apoptotic Process We were also interested in examining the activity of AAP-4 in an additional cell line. To this end, we have transfected human osteosarcoma-derived U2OS cells expressing wild-type p53 with plasmid pMT2SM-AAP-4 encoding the myc-tagged AAP-4 protein. As control, U2OS cells were transfected with the plasmid pCMV-LacZ encoding myc-tagged LacZ. Four or five days after transfection, the cells were fixed and analyzed for myc-tagged AAP-4 expression by means of immunofluorescence using the myc-tag specific antibody 9E10 and for apoptotic activity by DAPI staining. U2OS cells were stained aberrantly with DAPI, whereas the cells containing myc-tagged LacZ were not, which is indicative for induction of AAP-4-specific apoptosis.

These experiments were repeated three times and clearly showed that AAP-4 alone also kills U2OS tumor cells (FIG. 3). Thus, absence or presence of p53 is irrelevant for AAP-4 activity (like Apoptin), which broadens the tumor-target spectrum of AAP-4.

AAP-4 Localizes in Apoptotic Structures

One of the striking features of CA V-induced apoptosis is the "circular" Apoptin-positive structures occurring during the apoptotic process (Noteborn et al., 1994). These structures are visible in the nucleus at an early time point during apoptosis and become at a later stage more and more pronouncedly structured as circles or circular appearances or structures. We have now found that AAP-4 is located in the same "circular" structures as described for Apoptin. We have analyzed cells co-expressing both (myc-tagged) AAP-4 and Apoptin. Saos-2 cells were co-transfected with pMT2SN-AAP-4 and pCMV-Apoptin (Danen-van Oorschot, 1997). Indirect immunofluorescence, using both antibodies detecting AAP-4 or Apoptin and FITC- or rhodamine-labeled secondary antibody conjugates, was carried out as described by Danen-van Oorschot, 1997a, and proved that the "circular" structures contain both Apoptin and AAP-4 protein. Within these structures, Apoptin and AAP-4 partially co-localize with each other. It is the first cellular (derived from human (tumor) cells) protein that is associated with CAV- and/or Apoptin-associated apoptotic structures. A schematic representation of these structures is given in FIG. 4.

When AAP-4 was expressed alone in Saos-2 tumor cells, the staining pattern was diffusely punctuate nuclear staining in addition to large circular structures that lacked staining, giving the appearance of black holes in the nucleus. In contrast, normal VH10 cells expressing the AAP-4 construct showed only the diffuse nuclear staining, with no evidence for such black holes. These results strongly suggest a tumor-specific distribution of AAP-4 in the absence of Apoptin.

In conclusion, we have provided evidence that interference of specific factors with the function of AAP-4 proteins results in induction of apoptosis. Therapies based on induction of (p53-independent) apoptosis are possible utilizing the interference with the function of AAP-4 proteins. An example of such an interfering factor is Apoptin. Another CA V-derived protein, which is known to induce apoptosis and also known to enhance Apoptin activity, is VP2 (Noteborn et al., 1997).

Utility of AAP-4 Antisera

The best AAP-4 antibody of the two generated was selected for further use. We tested the efficacy of this antibody by transfecting primate COS-7 and human U2OS cells with the AAP-4-myc construct. Western analysis showed that the approximately 60-65 kDa AAP-4-myc protein was detected strongly only in samples where the DNA was transfected. Similarly, in immunoprecipitation experiments, AAP-4-myc was also strongly detected. Finally, we could detect the presence of AAP-4 in the nucleus using this AAP-4 antibody in immunofluorescence analysis.

Northern Blot Analysis

To examine whether AAP-4 was differentially expressed in tumor versus normal tissue, we tested a commercially available Northern blot (Invitrogen, cat. No. #D310001) that contained tumor and normal tissue derived from the same patient, from a variety of tissue types.

There was a very large RNA, approximately 6 to 7 kb, expressed in normal brain tissue that was not present in the same amount of RNA from uninvolved brain of the same patient. However, in the normal brain sample, we saw much smaller faint bands that might indicate the presence of splice variants.

Cloning and Sequence Analysis of Full-Length AAP-4

A further sequence analysis of the human AAP-4 DNA sequence yielded the 5690 bp-long nucleic acid sequence given in FIG. 5. An open reading frame was found in this nucleic acid sequence at position 236 to 2866. The deduced amino acid sequence is given in FIG. 6.

A protein domain called SET-domain was found in the amino acid sequence of the human AAP-4 protein. It spans the region of the amino acid 185 to amino acid 304.

The SET domain is a 130-amino acid, evolutionarily conserved sequence motif present in chromosomal proteins that function in modulating gene activities from yeast to mammals. Initially identified as members of the Polycomb- and trithorax-group (Pc-G and trx-G) gene families, these genes regulate the expression of the homeotic genes through a mechanism thought to involve some aspect of chromatin structure. Other proteins that have this motif also have additional domains or characteristics that support that suggestion that the SET domain is involved in chromatin-mediated gene regulation, and possibly in determining chromosome architecture. These observations implicate SET domain proteins as multifunctional chromatin regulators with activities in both eu- and heterochromatin (T. Jenuwein et al., 1998, *Cell. Mol. Life. Sci.* 54, 80-93).

Recently, it has been demonstrated that SET domains are protein-protein interaction domains important for the activity of multicomponent complexes involved in transcriptional activation or repression or phosphorylation (T. Rozovskaia et al., 2000, *Oncogene* 19, 351-357). SET domains are found in a number of proteins closely associated with human tumorigenesis, such as HRX/ALL1/MLL/Htrx, MOZ and MMSET, all of which are part of aberrant fusion proteins derived from chromosomal translocations found in a high percentage of human leukemias (S. Jacobson and L. Pillus 1999, *Curr. Opinion in Gen. & Dev.* 9, 175-184).

It was not until the present invention that such a SET domain was identified in an Apoptin-associating protein and, therefore, affecting the functional activity of the SET domain of AAP-4 should have therapeutic effects against tumors. The SET domain can be used to identify substances that bind to the SET domain. This would be done by methods known to persons skilled in the art, e.g., by binding studies, where an AAP-4 peptide comprising the SET domain is bound to a matrix and it is tested whether test substances bind to the AAP-4 peptide, or by co-immunoprecipitation of an AAP-4 peptide comprising the SET domain with test substances using antibodies generated against the AAP-4 peptide comprising the SET domain. Test substances are, for example, small organic compounds derived, e.g., from a compound library or peptides or proteins derived e.g. from a peptide library or from a natural source like a cell extract. The test substances are, for example, labeled for easier detection. The substances found to bind to the SET domain can either enhance or inhibit one or more effects of AAP-4. This is tested by measuring the apoptotic activity of AAP-4 as described above in the presence of the substances and by determining the nuclear localization of AAP-4 as described above in the presence of the substances.

All publications and patent applications mentioned in this specification are indicative of the level of skill of those skilled in the art to which this invention pertains. All publications, patents, and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

REFERENCES

1. Bellamy C. O. C., R. D. G. Malcomson, D. J. Harrison and H. Wyllie (1995). Cell death and disease: The biology and regulation of apoptosis. *Seminars in Cancer Biology* 6, 3-12.
2. Danen-Van Oorschot A. A. A. M., D. F. Fischer, J. M. Grimbergen, B. Klein, S.-M. Zhuang, J. H. F. Falkenburg, C. Backendorf, P. H. A. Quax, J. A. Van der Eb and M. H. M. Noteborn (1997). Apoptin induces apoptosis in human transformed and malignant cells but not in normal cells. *Proceedings National Academy Sciences, USA:* 94, 5843-5847.
3. Danen-Van Oorschot A. A. A. M, A. Den Hollander, S. Takayama, J. Reed, A. J. Van der Eb and M. H. M. Noteborn (1997a). BAG-1 inhibits p53-induced but not Apoptin-induced apoptosis. *Apoptosis* 2, 395-402.
4. Duke R. C., D. M. Ocjius, D. M. and J. D-E. Young (1996). Cell suicide in health and disease. *Scientific American* December 1996, 48-55.
5. Durfee T., K. Becherer, P.-L. Chen, S.-H. Yeh, Y. Yang, A. E. Kilburn, W.-H. Lee and S. J. Elledge (1993). The retinoblastoma protein associates with the protein phosphate type 1 catalytic subunit. *Genes and Development* 7, 555-569.
6. Earnshaw W. C. (1995). Nuclear changes in apoptosis. *Current Opinion in Cell Biology* 7, 337-343.
7. Fields S. and O. K. Song (1989). A novel genetic system to detect protein-protein interactions. *Nature* 340, 245-246.
8. Hockenberry D. M. (1994). Bcl-2 in cancer, development and apoptosis. *Journal of Cell Science*, Supplement 18, 51-55.
9. Hoffman C. S. and F. Winston (1987). A ten-minute DNA preparation from yeast efficiently releases autonomous plasmids for transformation of *Escherichia coli*. *Gene* 57, 267-272.
10. Kerr J. F. R., C. M. Winterford and B. V. Harmon (1994). Apoptosis: Its significance in cancer and cancer therapy. *Cancer* 73, 2013-2026.
11. Klebe R. J., J. V. Harriss, Z. D. Sharp and M. G. Douglas (1983). A general method for polyethylene-glycol-induced genetic transformation of bacteria and yeast. *Gene* 25, 333-341.
12. Levine A. J. (1997). p53, the cellular gatekeeper for growth and division. *Cell* 88, 323-331.
13. Maniatis T., E. F. Fritsch and J. Sambrook (1982). *Molecular Cloning: A Laboratory Manual*, CSHL Press, New York, USA.
14. McDonell T. J., R. E. Meyn and L. E. Robertson (1995). Implications of apoptotic cell death regulation in cancer therapy. *Seminars in Cancer Biology* 6, 53-60.
15. Noteborn M. H. M. (1996). PCT application WO 96/41191. Apoptin induces apoptosis in human transformed and malignant cells but not in normal cells as essential characteristic for the development of an antitumor therapy.
16. Noteborn M. H. M. and G. F. De Boer (1996). Patent USA/no. 030, 335.
17. Noteborn M. H. M., G. F. De Boer, D. Van Roozelaar, C. Karreman, O. Kranenburg, J. Vos, S. Jeurissen, A. Zantema, R. Hoeben, G. Koch, H. Van Ormondt and A. J. Van der Eb (1991). Characterization of cloned chicken anemia virus DNA that contains all elements for the infectious replication cycle. *Journal of Virology* 65, 3131-3139.
18. Notebom M. H. M. and A. Pietersen (1998). A gene delivery vehicle expressing the apoptosis-inducing proteins VP2 and/or Apoptin. PCT Application no. PCT/NL98/00213.
19. Noteborn M. H. M., D. Todd, C. A. J. Verschueren, H. W. F. M. De Gauw, W. L. Curran, S. Veldkamp, A. J. Douglas, M. S. McNulty, A. J. Van der Eb and G. Koch (1994). A single chicken anemia virus protein induces apoptosis. *Journal of Virology* 68, 346-351.
20. Noteborn M. H. M., C. A. J. Verschueren, G. Koch and A. J. Van der Eb (1998). Simultaneous expression of recombinant baculovirus-encoded chicken anemia virus (CAV) proteins VP1 and VP2 is required for formation of the CAV-specific neutralizing epitope. *Journal General Virology*, 79, 3073-3077.
21. Noteborn M. H. M. and Y. Zhang (1998). Methods and means for determining the transforming capability of agents, for determining the predisposition of cells to become transformed and prophylacetic treatment of cancer using Apoptin-like activity. PCT Application no. PCT/NL98/00457.
22. Noteborn M. H. M., A. A. M. Danen-van Oorschot and A. J. Van der Eb (1998a). Chicken anemia virus: Induction of apoptosis by a single protein of a single-stranded DNA virus. *Seminars in Virology* 8, 497-504.
23. Paulovich A. G., D. Toczyski and H. Hartwell (1997). When checkpoints fail. *Cell* 88, 315-321.
24. Pietersen A. M., M. M. Van der Eb, H. J. Rademaker, D. J. M. Van den Wollenberg, M. J. W. E. Rabelink, P. J. K. Kuppen, J. H. Van Dierendonck, H. Van Ormondt, D. Masman, C. J. H. Van de Velde, A. J. Van der Eb, R. C. Hoeben and M. H. M. Notebom (1999). Specific tumor cell killing with adenovirus vectors containing the Apoptin gene. *Gene Therapy* 6, 882-892.
25. Rose M. D., F. Winston and P. Hieter (1990). *Methods in yeast genetics. A laboratory course manual*. Cold Spring Harbor Laboratory Press, Cold Spring Harbor, N.Y., USA.
26. Sachs L. and J. Lotem (1993). Control of programmed cell death in normal and leukemia cells: New implications for therapy. *Blood* 82, 15-21.
27. Sanger F., S. Nicklen and A. R. Coulsen (1977). DNA sequencing with chain-terminating inhibitors. *Proceedings National Academic Sciences USA* 74, 5463-5467.
28. Steller H. (1995). Mechanisms and genes of cellular suicide. *Science* 267, 1445-1449.
29. Telford W. G., L. E. King and P. J. Fraker (1992). Comparative evaluation of several DNA binding dyes in the detection of apoptosis-associated chromatin degradation by flow cytometry. *Cytometry* 13, 137-143.
30. Teodoro J. G. and P. E. Branton (1997). Regulation of apoptosis by viral gene products. *Journal of Virology* 71, 1739-1746.

31. Thompson C. B. (1995). Apoptosis in the pathogenesis and treatment of disease. *Science* 267, 1456-1462.
32. White E. (1996). Life, death, and the pursuit of apoptosis. *Genes and development* 10, 1-15.
33. Wyllie A. H. (1995). The genetic regulation of apoptosis. *Current Opinion in Genetics and Development* 5, 97-104.
34. Wyllie A. H., J. F. R. Kerr and A. R. Currie (1980). Cell death: The significance of apoptosis. *International Review of Cytology* 68, 251-306.
35. Yang X., E. J. A. Hubbard and M. Carlson (1992). A protein kinase substrate identified by the two-hybrid system. *Science* 257, 680-682.
36. Zhuang S.-M., J. E. Landegent, C. A. J. Verschueren, J. H. F. Falkenburg, H. Van Ormondt, A. J. Van der Eb and M. H. M. Noteborn (1995). Apoptin, a protein encoded by chicken anemia virus, induces cell death in various human hematologic malignant cells in vitro. *Leukemia* 9 S1, 118-120.
37. Zhuang S.-M., A. Shvarts, H. Van Ormondt, A.-G. Jochemsen, A. J. Van der Eb and M. H. M. Noteborn (1995). Apoptin, a protein derived from chicken anemia virus, induces a p53-independent apoptosis in human osteosarcoma cells. *Cancer Research* 55, 486-489.
38. Evans G. I., G. K. Lewis, G. Ramsay and J. M. Bishop (1985). Isolation of monoclonal antibodies specific for human c-myc proto-oncogene product. *Mol. Cell. Biol. Dec.* 5 (12), 3610-3616
39. T. Jenuwein et al. (1998). *Cell. Mol. Life. Sci.* 54, 80-93.
40. T. Rozovskaia et al. (2000). *Oncogene* 19, 351-357.
41. S. Jacobson and L. Pillus (1999). *Curr. Opinion in Gen. & Dev.* 9, 175-184.

What is claimed is:

1. An isolated or recombinant proteinaceous substance encoded by SEQ ID NO:13 or by a nucleic acid at least 90% homologous to the nucleic acid sequence of SEQ ID NO:10.

2. An isolated or recombinant proteinaceous substance comprising an amino acid sequence at least 90% homologous to SEQ ID NO:12.

3. An isolated or synthetic antibody that specifically recognizes a proteinaceous substance comprising an amino acid sequence at least 90% homologous to SEQ ID NO:12.

4. A proteinaceous substance specifically recognized by the antibody of claim 3, wherein said proteinaceous substance localizes to the nucleus of a cell and induces apoptosis.

5. A method of inducing apoptosis in a cell, said method comprising:
   providing a host cell with a nucleic acid that encodes a proteinaceous substance comprising an amino acid sequence at least 90% homologous to SEQ ID NO:12, so that apoptosis is induced in the host cell.

6. The method according to claim 5, wherein said apoptosis is p53-independent.

7. The method according to claim 6, further comprising: providing said host cell with a nucleic acid encoding Apoptin.

8. A method of inducing apoptosis, said method comprising:
   providing a host cell with a proteinaceous substance that comprises an amino acid sequence at least 90% homologous to SEQ ID NO: 12, whereby apoptosis is induced.

9. The method according to claim 8, wherein said apoptosis is p53-independent.

10. The method according to claim 9, further comprising: providing said host cell with an Apoptin.

11. A method of treating a disease where enhanced cell proliferation or decreased cell death is observed in an individual, said method comprising:
    providing an individual in need thereof with a pharmaceutical composition comprising a proteinaceous substance that comprises an amino acid sequence at least 90% homologous to SEQ ID NO:12,
so that said disease is treated.

12. The method according to claim 11, wherein said pharmaceutical composition further comprises an Apoptin.

13. The method according to claim 11, wherein said disease comprises a cancer or an autoimmune disease.

14. An isolated or recombinant proteinaceous substance encoded by a nucleic acid selected from the group consisting of SEQ ID NO:13, a nucleic acid at least 90% homologous to the nucleic acid sequence of SEQ ID NO: 10, and combinations thereof.

* * * * *

SEQUENCE LISTING

<160> NUMBER OF SEQ ID NOS: 15

<210> SEQ ID NO 1
<211> LENGTH: 17
<212> TYPE: DNA
<213> ORGANISM: Artificial Sequence
<220> FEATURE:
<223> OTHER INFORMATION: pACT-primer

<400> SEQUENCE: 1
taccactaca atggatg                                                    17

<210> SEQ ID NO 2
<211> LENGTH: 15
<212> TYPE: PRT
<213> ORGANISM: Artificial Sequence
<220> FEATURE:
<223> OTHER INFORMATION: peptides to generate polyclonal antibodies
<220> FEATURE:
<221> NAME/KEY: SITE
<222> LOCATION: (1)..(15)
<223> OTHER INFORMATION:

<400> SEQUENCE: 2

Glu Glu Ser Thr Pro Val His Asp Ser Pro Gly Lys Asp Asp Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: peptides to generate polyclonal antibodies
<220> FEATURE:
<221> NAME/KEY: SITE
<222> LOCATION: (1)..(15)
<223> OTHER INFORMATION:

<400> SEQUENCE: 3

Asp Ser Phe Lys Thr Lys Asp Ser Phe Arg Thr Ala Lys Ser Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: peptides to generate polyclonal antibodies
<220> FEATURE:

```
<221> NAME/KEY: SITE
<222> LOCATION: (1)..(15)
<223> OTHER INFORMATION:

<400> SEQUENCE: 4

Ile Asp Ile Asp Ile Ser Ser Arg Arg Arg Glu Asp Gln Ser Leu
1               5                   10                  15

<210> SEQ ID NO 5
<211> LENGTH: 29
<212> TYPE: DNA
<213> ORGANISM: Artificial Sequence
<220> FEATURE:
<223> OTHER INFORMATION: primer AAP-4#3F

<400> SEQUENCE: 5
gtcagctcta acactgatgc agataccac                                    29

<210> SEQ ID NO 6
<211> LENGTH: 29
<212> TYPE: DNA
<213> ORGANISM: Artificial Sequence
<220> FEATURE:
<223> OTHER INFORMATION: primer AAP-4#3R

<400> SEQUENCE: 6
gtggtatctg catcagtgtt agagctgac                                    29

<210> SEQ ID NO 7
<211> LENGTH: 28
<212> TYPE: DNA
<213> ORGANISM: Artificial Sequence
<220> FEATURE:
<223> OTHER INFORMATION: primer AAP-4#8F

<400> SEQUENCE: 7
gagagtgact aaatgcacct gggtcagg                                     28

<210> SEQ ID NO 8
<211> LENGTH: 24
<212> TYPE: DNA
<213> ORGANISM: Artificial Sequence
<220> FEATURE:
<223> OTHER INFORMATION: primer AAP-4#9R

<400> SEQUENCE: 8
gttatcccag gtcaagttaa gacc                                         24

<210> SEQ ID NO 9
<211> LENGTH: 10
<212> TYPE: PRT
<213> ORGANISM: Artificial Sequence
<220> FEATURE:
<223> OTHER INFORMATION: Myc-tag
<220> FEATURE:
<221> NAME/KEY: SITE
<222> LOCATION: (1)..(10)
<223> OTHER INFORMATION:

<400> SEQUENCE: 9

Glu Gln Lys Leu Ile Ser Glu Glu Asp Leu
1               5                   10

<210> SEQ ID NO 10
<211> LENGTH: 770
<212> TYPE: DNA
<213> ORGANISM: Homo sapiens
```

```
<220> FEATURE:
<221> NAME/KEY: CDS
<222> LOCATION: (12)..(512)
<223> OTHER INFORMATION:
<220> FEATURE:
<221> NAME/KEY: misc_feature
<223> OTHER INFORMATION: Description of Combined DNA/RNA Molecule:
      sequence of AAP-4

<400> SEQUENCE: 10
gccacgaagg c cgg gag agc tcg ccc tgc acc tac ata act cgg cgg tca      50
            Arg Glu Ser Ser Pro Cys Thr Tyr Ile Thr Arg Arg Ser
             1               5                  10 gtg agg aca aga aca aat ctg aag gag gcc tct gac atc aag ctt gaa      98
Val Arg Thr Arg Thr Asn Leu Lys Glu Ala Ser Asp Ile Lys Leu Glu
 15              20                  25 cca aat acg ttg aat ggc tat aaa agc agt gtg acg gaa cct tgc ccc     146
Pro Asn Thr Leu Asn Gly Tyr Lys Ser Ser Val Thr Glu Pro Cys Pro
30              35                  40                  45 gac agt ggt gaa cag ctg cag cca gct cct gtg ctg cag gag gaa gaa     194
Asp Ser Gly Glu Gln Leu Gln Pro Ala Pro Val Leu Gln Glu Glu Glu
                50                  55                  60 ctg gct cat gag act gca caa aaa ggg gag gca aag tgt cat aag agt     242
Leu Ala His Glu Thr Ala Gln Lys Gly Glu Ala Lys Cys His Lys Ser
             65                  70                  75 gac aca ggc atg tcc aaa aag aag tca cga caa gga aaa ctt gtg aaa     290
Asp Thr Gly Met Ser Lys Lys Lys Ser Arg Gln Gly Lys Leu Val Lys
 80                  85                  90 cag ttt gca aaa ata gag gaa tct act cca gtg cac gat tct cct gga     338
Gln Phe Ala Lys Ile Glu Glu Ser Thr Pro Val His Asp Ser Pro Gly
 95                 100                 105 aaa gac gac gcg gta cca gat ttg atg ggt ccc cat tct gac cag ggt     386
Lys Asp Asp Ala Val Pro Asp Leu Met Gly Pro His Ser Asp Gln Gly
110                 115                 120                 125 gag cac agt ggc act gtg ggc gtg cct gtg agc tac aca gac tgt gct     434
Glu His Ser Gly Thr Val Gly Val Pro Val Ser Tyr Thr Asp Cys Ala
                130                 135                 140 cct tca ccc gtc ggt tgt tca gtt gtg aca tca gat agc ttc aaa aca     482
Pro Ser Pro Val Gly Cys Ser Val Val Thr Ser Asp Ser Phe Lys Thr
            145                 150                 155 aaa gac agc ttt aga act gca aaa aag taa aagaagagg cgaatcacaa        532
Lys Asp Ser Phe Arg Thr Ala Lys Lys
                160                 165 ggtatgatgc acagttaatc ctagaaaata actctgggag tcccaaattg actcttcgta   592
ggcgtcatga tagcagcagc aaaacaaatg gaccaagaga atgatgggaa tgaaactctt   652
cccaaaatta agcatcaagt ttaagccaaa gaccatgaca acgataacaa tctcgatgta   712
gcaaagttat aagggtttag ctcaggatta ggaatgtttc acaaaattaa aaaggcat    770

<210> SEQ ID NO 11
<211> LENGTH: 166
<212> TYPE: PRT
<213> ORGANISM: Homo sapiens
<220> FEATURE:
<221> NAME/KEY: misc_feature
<223> OTHER INFORMATION: Description of Combined DNA/RNA Molecule:
      sequence of AAP-4

<400> SEQUENCE: 11

Arg Glu Ser Ser Pro Cys Thr Tyr Ile Thr Arg Arg Ser Val Arg Thr
 1               5                  10                  15

Arg Thr Asn Leu Lys Glu Ala Ser Asp Ile Lys Leu Glu Pro Asn Thr
```

```
                    20                  25                  30
Leu Asn Gly Tyr Lys Ser Ser Val Thr Glu Pro Cys Pro Asp Ser Gly
            35                  40                  45

Glu Gln Leu Gln Pro Ala Pro Val Leu Gln Glu Glu Leu Ala His
        50                  55                  60

Glu Thr Ala Gln Lys Gly Glu Ala Lys Cys His Lys Ser Asp Thr Gly
65                  70                  75                  80

Met Ser Lys Lys Lys Ser Arg Gln Gly Lys Leu Val Lys Gln Phe Ala
                85                  90                  95

Lys Ile Glu Glu Ser Thr Pro Val His Asp Ser Pro Gly Lys Asp Asp
            100                 105                 110

Ala Val Pro Asp Leu Met Gly Pro His Ser Asp Gln Gly Glu His Ser
            115                 120                 125

Gly Thr Val Gly Val Pro Val Ser Tyr Thr Asp Cys Ala Pro Ser Pro
        130                 135                 140

Val Gly Cys Ser Val Val Thr Ser Asp Ser Phe Lys Thr Lys Asp Ser
145                 150                 155                 160

Phe Arg Thr Ala Lys Lys
                165

<210> SEQ ID NO 12
<211> LENGTH: 256
<212> TYPE: PRT
<213> ORGANISM: Homo sapiens
<220> FEATURE:
<221> NAME/KEY: SITE
<222> LOCATION: (1)..(256)
<223> OTHER INFORMATION: /note="Amino-acid sequence of the analyse
      region of the Apoptin-associating clone AAP-4, wherein X is a
      stopcodon"
<220> FEATURE:
<221> NAME/KEY: misc_feature
<222> LOCATION: (170)..(247)
<223> OTHER INFORMATION: Xaa can be any amino acid

<400> SEQUENCE: 12

His Glu Gly Arg Glu Ser Ser Pro Cys Thr Tyr Ile Thr Arg Arg Ser
1               5                   10                  15

Val Arg Thr Arg Thr Asn Leu Lys Glu Ala Ser Asp Ile Lys Leu Glu
            20                  25                  30

Pro Asn Thr Leu Asn Gly Tyr Lys Ser Ser Val Thr Glu Pro Cys Pro
        35                  40                  45

Asp Ser Gly Glu Gln Leu Gln Pro Ala Pro Val Leu Gln Glu Glu Glu
    50                  55                  60

Leu Ala His Glu Thr Ala Gln Lys Gly Glu Ala Lys Cys His Lys Ser
65                  70                  75                  80

Asp Thr Gly Met Ser Lys Lys Lys Ser Arg Gln Gly Lys Leu Val Lys
                85                  90                  95

Gln Phe Ala Lys Ile Glu Glu Ser Thr Pro Val His Asp Ser Pro Gly
            100                 105                 110

Lys Asp Asp Ala Val Pro Asp Leu Met Gly Pro His Ser Asp Gln Gly
        115                 120                 125

Glu His Ser Gly Thr Val Gly Val Pro Val Ser Tyr Thr Asp Cys Ala
    130                 135                 140

Pro Ser Pro Val Gly Cys Ser Val Val Thr Ser Asp Ser Phe Lys Thr
145                 150                 155                 160

Lys Asp Ser Phe Arg Thr Ala Lys Lys Xaa Lys Glu Glu Ala Asn His
                165                 170                 175
```

-continued

```
Lys Val Xaa Cys Thr Val Asn Pro Arg Lys Xaa Leu Trp Glu Ser Gln
            180                 185                 190

Ile Asp Ser Ser Xaa Ala Ser Xaa Xaa Gln Gln Gln Asn Lys Trp Thr
        195                 200                 205

Lys Arg Met Met Gly Met Lys Leu Phe Pro Lys Leu Ser Ile Lys Phe
        210                 215                 220

Lys Pro Lys Thr Met Thr Thr Ile Thr Ile Ser Met Xaa Gln Ser Tyr
225                 230                 235                 240

Lys Gly Leu Ala Gln Asp Xaa Glu Cys Phe Thr Lys Leu Lys Arg His
            245                 250                 255
```

<210> SEQ ID NO 13
<211> LENGTH: 5690
<212> TYPE: DNA
<213> ORGANISM: Homo sapiens
<220> FEATURE:
<221> NAME/KEY: CDS
<222> LOCATION: (236)..(2866)
<223> OTHER INFORMATION:

<400> SEQUENCE: 13

```
cggcagggca gcggggcgat gaggtgagga cgcccgggaa ccggaggcgg caccgcgcgg      60
cgcacggacc tgggacgcgg agtcctgaag ccggcggacg gttttcgtac gggcggccgt     120
gcgcgaggcg aggagagaac attgaaagta ttctctaagc tatttgaaga gagtgactaa     180
atgcacctgg gtcaggctgt ctgtgggtat gaagtggttg ggagaatcca agaac atg     238
                                                              Met
                                                                1 gtg gtg aat ggc agg aga aat gga ggc aag ttg tct aat gac cat cag     286
Val Val Asn Gly Arg Arg Asn Gly Gly Lys Leu Ser Asn Asp His Gln
      5                  10                  15 cag aat caa tca aaa tta cag cac acg ggg aag gac acc ctg aag gct     334
Gln Asn Gln Ser Lys Leu Gln His Thr Gly Lys Asp Thr Leu Lys Ala
 20                  25                  30 ggc aaa aat gca gtc gag agg agg tcg aac aga tgt aat ggt aac tcg     382
Gly Lys Asn Ala Val Glu Arg Arg Ser Asn Arg Cys Asn Gly Asn Ser
 35                  40                  45 gga ttt gaa gga cag agt cgc tat gta cca tcc tct gga atg tcc gcc     430
Gly Phe Glu Gly Gln Ser Arg Tyr Val Pro Ser Ser Gly Met Ser Ala
 50              55                  60                  65 aag gaa ctc tgt gaa aat gat gac cta gca acc agt ttg gtt ctt gat     478
Lys Glu Leu Cys Glu Asn Asp Asp Leu Ala Thr Ser Leu Val Leu Asp
             70                  75                  80 ccc tat tta ggt ttt caa aca cac aaa atg aat act agc gcc ttt cct     526
Pro Tyr Leu Gly Phe Gln Thr His Lys Met Asn Thr Ser Ala Phe Pro
         85                  90                  95 tcg agg agc tca agg cat ttt tca aaa tct gac agt ttt tct cac aac     574
Ser Arg Ser Ser Arg His Phe Ser Lys Ser Asp Ser Phe Ser His Asn
        100                 105                 110 aac cct gtg aga ttt agg cct att aaa gga agg cag gaa gaa cta aag     622
Asn Pro Val Arg Phe Arg Pro Ile Lys Gly Arg Gln Glu Glu Leu Lys
    115                 120                 125 gaa gta att gaa cgt ttt aag aaa gat gaa cac ttg gag aaa gcc ttc     670
Glu Val Ile Glu Arg Phe Lys Lys Asp Glu His Leu Glu Lys Ala Phe
130                 135                 140                 145 aaa tgt ttg act tca ggc gaa tgg gca cgg cac tat ttt ctc aac aag     718
Lys Cys Leu Thr Ser Gly Glu Trp Ala Arg His Tyr Phe Leu Asn Lys
             150                 155                 160 aat aaa atg cag gag aaa tta ttc aaa gaa cat gta ttt att tat ttg     766
```

```
                Asn Lys Met Gln Glu Lys Leu Phe Lys Glu His Val Phe Ile Tyr Leu
                            165                 170                 175 cga atg ttt gca act gac agt gga ttt gaa ata ttg cca tgt aat aga         814
Arg Met Phe Ala Thr Asp Ser Gly Phe Glu Ile Leu Pro Cys Asn Arg
            180                 185                 190 tac tca tca gaa caa aat gga gcc aaa ata gtt gca aca aaa gag tgg         862
Tyr Ser Ser Glu Gln Asn Gly Ala Lys Ile Val Ala Thr Lys Glu Trp
    195                 200                 205 aaa cga aat gac aaa ata gaa tta ctg gtg ggt tgt att gcc gaa ctt         910
Lys Arg Asn Asp Lys Ile Glu Leu Leu Val Gly Cys Ile Ala Glu Leu
210                 215                 220                 225 tca gaa att gag gag aac atg cta ctt aga cat gga gaa aac gac ttc         958
Ser Glu Ile Glu Glu Asn Met Leu Leu Arg His Gly Glu Asn Asp Phe
                230                 235                 240 agt gtc atg tac tcc aca agg aaa aac tgt gct caa ctc tgg ctg ggt        1006
Ser Val Met Tyr Ser Thr Arg Lys Asn Cys Ala Gln Leu Trp Leu Gly
            245                 250                 255 cct gct gcg ttt ata aac cat gat tgc aga cct aat tgt aag ttt gtg        1054
Pro Ala Ala Phe Ile Asn His Asp Cys Arg Pro Asn Cys Lys Phe Val
    260                 265                 270 tca act ggt cga gat aca gca tgt gtg aag gct cta aga gac att gaa        1102
Ser Thr Gly Arg Asp Thr Ala Cys Val Lys Ala Leu Arg Asp Ile Glu
275                 280                 285 cct gga gaa gaa att tct tgt tat tat gga gat ggg ttc ttt gga gaa        1150
Pro Gly Glu Glu Ile Ser Cys Tyr Tyr Gly Asp Gly Phe Phe Gly Glu
290                 295                 300                 305 aat aat gag ttc tgc gag tgt tac act tgc gaa aga cgg ggc act ggt        1198
Asn Asn Glu Phe Cys Glu Cys Tyr Thr Cys Glu Arg Arg Gly Thr Gly
                310                 315                 320 gct ttt aaa tcc aga gtg gga ctg cct gcg cct gct cct gtt atc aat        1246
Ala Phe Lys Ser Arg Val Gly Leu Pro Ala Pro Ala Pro Val Ile Asn
            325                 330                 335 agc aaa tat gga ctc aga gaa aca gat aaa cgt tta aat agg ctt aaa        1294
Ser Lys Tyr Gly Leu Arg Glu Thr Asp Lys Arg Leu Asn Arg Leu Lys
    340                 345                 350 aag tta ggt gac agc agc aaa aat tca gac agt caa tct gtc agc tct        1342
Lys Leu Gly Asp Ser Ser Lys Asn Ser Asp Ser Gln Ser Val Ser Ser
355                 360                 365 aac act gat gca gat acc act cag gaa aaa aac aat gca act tct aac        1390
Asn Thr Asp Ala Asp Thr Thr Gln Glu Lys Asn Asn Ala Thr Ser Asn
370                 375                 380                 385 cga aaa tct tca gtt ggc gta aaa aag aat agc aag agc aga acg tta        1438
Arg Lys Ser Ser Val Gly Val Lys Lys Asn Ser Lys Ser Arg Thr Leu
                390                 395                 400 acg agg caa tct atg tca aga att cca gct tct tcc aac tct acc tca        1486
Thr Arg Gln Ser Met Ser Arg Ile Pro Ala Ser Ser Asn Ser Thr Ser
            405                 410                 415 tct aag cta act cat ata aat aat tcc agg gta cca aag aaa ctg aag        1534
Ser Lys Leu Thr His Ile Asn Asn Ser Arg Val Pro Lys Lys Leu Lys
    420                 425                 430 aag cct gca aag cct tta ctt tca aag ata aaa ttg aga aat cat tgc        1582
Lys Pro Ala Lys Pro Leu Leu Ser Lys Ile Lys Leu Arg Asn His Cys
435                 440                 445 aag cgg ctg gag caa aag aat gct tca aga aaa ctc gaa atg gga aac        1630
Lys Arg Leu Glu Gln Lys Asn Ala Ser Arg Lys Leu Glu Met Gly Asn
450                 455                 460                 465 tta gta ctg aaa gag cct aaa gta gtt ctg tat aaa aat ttg ccc att        1678
Leu Val Leu Lys Glu Pro Lys Val Val Leu Tyr Lys Asn Leu Pro Ile
                470                 475                 480
```

```
aaa aaa gat aag gag cca gag gga cca gcc caa gcc gca gtt gcc agc    1726
Lys Lys Asp Lys Glu Pro Glu Gly Pro Ala Gln Ala Ala Val Ala Ser
            485                 490                 495 ggg tgc ttg act aga cac gcg gcg aga gaa cac aga cag aat cct gtg    1774
Gly Cys Leu Thr Arg His Ala Ala Arg Glu His Arg Gln Asn Pro Val
        500                 505                 510 aga ggt gct cat tcg cag ggg gag agc tcg ccc tgc acc tac ata act    1822
Arg Gly Ala His Ser Gln Gly Glu Ser Ser Pro Cys Thr Tyr Ile Thr
515                 520                 525 cgg cgg tca gtg agg aca aga aca aat ctg aag gag gcc tct gac atc    1870
Arg Arg Ser Val Arg Thr Arg Thr Asn Leu Lys Glu Ala Ser Asp Ile
530                 535                 540                 545 aag ctt gaa cca aat acg ttg aat ggc tat aaa agc agt gtg acg gaa    1918
Lys Leu Glu Pro Asn Thr Leu Asn Gly Tyr Lys Ser Ser Val Thr Glu
                550                 555                 560 cct tgc ccc gac agt ggt gaa cag ctg cag cca gct cct gtg ctg cag    1966
Pro Cys Pro Asp Ser Gly Glu Gln Leu Gln Pro Ala Pro Val Leu Gln
            565                 570                 575 gag gaa gaa ctg gct cat gag act gca caa aaa ggg gag gca aag tgt    2014
Glu Glu Glu Leu Ala His Glu Thr Ala Gln Lys Gly Glu Ala Lys Cys
        580                 585                 590 cat aag agt gac aca ggc atg tcc aaa aag aag tca cga caa gga aaa    2062
His Lys Ser Asp Thr Gly Met Ser Lys Lys Lys Ser Arg Gln Gly Lys
595                 600                 605 ctt gtg aaa cag ttt gca aaa ata gag gaa tct act cca gtg cac gat    2110
Leu Val Lys Gln Phe Ala Lys Ile Glu Glu Ser Thr Pro Val His Asp
610                 615                 620                 625 tct cct gga aaa gac gac gcg gta cca gat ttg atg ggt ccc cat tct    2158
Ser Pro Gly Lys Asp Asp Ala Val Pro Asp Leu Met Gly Pro His Ser
                630                 635                 640 gac cag ggt gag cac agt ggc act gtg ggc gtg cct gtg agc tac aca    2206
Asp Gln Gly Glu His Ser Gly Thr Val Gly Val Pro Val Ser Tyr Thr
            645                 650                 655 gac tgt gct cct tca ccc gtc ggt tgt tca gtt gtg aca tca gat agc    2254
Asp Cys Ala Pro Ser Pro Val Gly Cys Ser Val Val Thr Ser Asp Ser
        660                 665                 670 ttc aaa aca aaa gac agc ttt aga act gca aaa agt aaa aag aag agg    2302
Phe Lys Thr Lys Asp Ser Phe Arg Thr Ala Lys Ser Lys Lys Lys Arg
675                 680                 685 cga atc aca agg tat gat gca cag tta atc cta gaa aat aac tct ggg    2350
Arg Ile Thr Arg Tyr Asp Ala Gln Leu Ile Leu Glu Asn Asn Ser Gly
690                 695                 700                 705 att ccc aaa ttg act ctt cgt agg cgt cat gat agc agc agc aaa aca    2398
Ile Pro Lys Leu Thr Leu Arg Arg Arg His Asp Ser Ser Ser Lys Thr
                710                 715                 720 aat gac caa gag aat gat gga atg aac tct tcc aaa ata agc atc aag    2446
Asn Asp Gln Glu Asn Asp Gly Met Asn Ser Ser Lys Ile Ser Ile Lys
            725                 730                 735 tta agc aaa gac cat gac aac gat aac aat ctc tat gta gca aag ctt    2494
Leu Ser Lys Asp His Asp Asn Asp Asn Asn Leu Tyr Val Ala Lys Leu
        740                 745                 750 aat aat gga ttt aac tca gga tca ggc agt agt tct aca aaa tta aaa    2542
Asn Asn Gly Phe Asn Ser Gly Ser Gly Ser Ser Ser Thr Lys Leu Lys
755                 760                 765 atc cag cta aaa cga gat gag gaa aat agg ggg tct tat aca gag ggg    2590
Ile Gln Leu Lys Arg Asp Glu Glu Asn Arg Gly Ser Tyr Thr Glu Gly
770                 775                 780                 785 ctt cat gaa aat ggg gtg tgc tgc agt gat cct ctt tct ctc ttg gag    2638
Leu His Glu Asn Gly Val Cys Cys Ser Asp Pro Leu Ser Leu Leu Glu
                790                 795                 800
```

| | | |
|---|---|---|
| tct cga atg gag gtg gat gac tat agt cag tat gag gaa gaa agt aca<br>Ser Arg Met Glu Val Asp Asp Tyr Ser Gln Tyr Glu Glu Glu Ser Thr<br>          805                    810                    815 | | 2686 |
| gat gat tcc tcc tct tct gag ggc gat gaa gag gag gat gac tat gat<br>Asp Asp Ser Ser Ser Ser Glu Gly Asp Glu Glu Glu Asp Asp Tyr Asp<br>          820                    825                    830 | | 2734 |
| gat gac ttt gaa gac gat ttt att cct ctt cct cca gct aag cgc ttg<br>Asp Asp Phe Glu Asp Asp Phe Ile Pro Leu Pro Pro Ala Lys Arg Leu<br>835                    840                    845 | | 2782 |
| agg tta ata gtt gga aaa gac tct ata gat att gac att tct tca agg<br>Arg Leu Ile Val Gly Lys Asp Ser Ile Asp Ile Asp Ile Ser Ser Arg<br>850                    855                    860                    865 | | 2830 |
| aga aga gaa gat cag tct tta agg ctt aat gcc taa gctcttggtc<br>Arg Arg Glu Asp Gln Ser Leu Arg Leu Asn Ala<br>                   870                    875 | | 2876 |
| ttaacttgac ctgggataac tactttaaag aaataaaaaa ttccagtcaa ttattcctca | | 2936 |
| actgaaagtt tagtggcagc acttctattg tcccttcact tatcagcata ctattgtaga | | 2996 |
| aagtgtacag catactgact caattcttaa gtctgatttg tgcaaatttt tatcgtactt | | 3056 |
| tttaaatagc cttcttacgt gcaattctga gttagaggta aagccctgtt gtaaaataaa | | 3116 |
| ggctcaagca aaattgtaca gtgatagcaa cttccacac aggacgttga aaacagtaat | | 3176 |
| gtggctacac agttttttta actgtaagag catcagctgg ctctttaata tatgactaaa | | 3236 |
| caataattta aaacaaatca tagtagcagc atattaaggg tttctagtat gctaatatca | | 3296 |
| ccagcaatga tctttggctt tttgatttat ttgctagatg tttccccctt ggagttttgt | | 3356 |
| cagtttcaca ctgtttgctg gcccaggtgt actgtttgtg cctttgtta atatcgcaaa | | 3416 |
| ccattggttg ggagtcagat tggtttctta aaaaaaaaa aaaatgaca tacgtgacag | | 3476 |
| ctcactttc agttcattat atgtacgagg gtagcagtgt gtgggatgag gttcgataca | | 3536 |
| gcgtatttat tgcttgtcat gtaaattaaa aaccttgtat ttaactcttt tcaatccttt | | 3596 |
| tagataaaat tgttctttgc aagaatgatt ggtgcttatt ttttcaaaaa tttgctgtga | | 3656 |
| acaacgtgat gacaacaagc aacatttatc taatgaacta cagctatctt aatttggttc | | 3716 |
| ttcaagtttt ctgttgcact tgtaaaatgc tacaaggaat attaaaaaaa tctattcact | | 3776 |
| ttaacttata atagtttatg aaataaaaac atgagtcaca gcttttgttc tgtggtaacc | | 3836 |
| tataaaaaaa gtttgtcttt gagattcaat gtaaagaact gaaacaatg tatatgttgt | | 3896 |
| aaatatttgt gtgttgtgag acattttgt cataagaaat taaagaact taccaggaag | | 3956 |
| gttttaagt ttagaaatat tcatgccaat aaaataggaa attataaata tatagtttta | | 4016 |
| agcactgcat cagtgggagt tcttggctta tgttagttta tgttagttta ttatgaaaac | | 4076 |
| atcaaagatt tttttgacta tattatcagt taaacaaaaa ggagtcagat ttaatttgtt | | 4136 |
| ttttgaagca ctttgagaaa ttaattttaa ttaacttaat gagcaaattt ttattactac | | 4196 |
| tttatgttca ataccaggtt cttttcattt ctctggatta ttttgcaaat cattggacag | | 4256 |
| agaatttggg aatataaatc tgtaacaggt gttgacacca gtaggtctct ttatttctgg | | 4316 |
| gaaatgtgta cctgtacttt ctgatataca gtgttcctaa gtaaaaatca attcagggga | | 4376 |
| tttgtatagt gtctatagga aagtagccca tgtcttgaaa tatgaaaagg aatctgaagg | | 4436 |
| tcatgaaaag tccagtggag aaaatctcaa tgcttactgt tactactaat tgattcctac | | 4496 |
| tagtttccag gtttgggggg atattgtttc aatgacgctc cttaagactg ttgattgccc | | 4556 |
| ataggttcca aatagaaatt aagactcatg aacattttta gaaagtagat tgttttctcc | | 4616 |

```
tggttctcta aggaactact tctgcagtct tacatagtct catccttgtt tgttgtggtg    4676
cagtcgaact cctcaggcgt ttggaaagca tgtggtagac cttcttccac acccacccat    4736
accccgttc actgcgtctg gaggtcttca acagtgaagt agggcagccc acacagcctc     4796
tcaggagcac ctgtccgagg cacccggagc actttgcaga gcacgtccag ccctcatggg    4856
gtccctgcat agaaatgtga acccctgcca ctgaggaaga tgaaggtaga ccctgtgtct    4916
ggaggtgctg gagggcagcg ggtcacctct tgtattccca ccttagtttg gggtgttttg    4976
aagaggttca gagactaaat cttaaacctt atttgaatac caacgatagc tatttggga    5036
atttcgatct taaaaagtga caaaacacat ttcccatttt catttttcag ctgaatttta    5096
gtaacttatt tttgatgttt taatttatc atggcctcct ctttggaggc caaccttccc    5156
atgggtctca aagcagtgac atttggtagt aaatcactgc ctctcaggag tcggtatgca    5216
caagcactca gcagccactg ttgatgcctt ctagggaaac ctaatttccg ttggtaaagg    5276
tagggggcctc ggaactgttc cggatctgct gtagaacttc accgtgtgga atggtgacag   5336
ccacacaccg ttgaccagtt tagaagaggt tgcattcaat aaaactctta gcttgagctt    5396
atgcaatgat tggttaagat tttggcattg taagaattag gagatgatca tagaaatata    5456
tgtaaagtat tcaattttca atcattttca aattactgtt ataaattgtt tttgctgagt    5516
tgtaatactt ttgagataca atgtattcct tgtactgaaa gaatgaaaaa ggactttttc    5576
agcatttgag gtaagttctt taacgtttca ttaaaaacat ttttacaaa tattttgtac     5636
atgcacttgc agtattgagg ttaatcattt taataaattc ggaaattaaa aaaa           5690

<210> SEQ ID NO 14
<211> LENGTH: 876
<212> TYPE: PRT
<213> ORGANISM: Homo sapiens

<400> SEQUENCE: 14

Met Val Val Asn Gly Arg Arg Asn Gly Gly Lys Leu Ser Asn Asp His
1               5                   10                  15

Gln Gln Asn Gln Ser Lys Leu Gln His Thr Gly Lys Asp Thr Leu Lys
            20                  25                  30

Ala Gly Lys Asn Ala Val Glu Arg Arg Ser Asn Arg Cys Asn Gly Asn
        35                  40                  45

Ser Gly Phe Glu Gly Gln Ser Arg Tyr Val Pro Ser Ser Gly Met Ser
    50                  55                  60

Ala Lys Glu Leu Cys Glu Asn Asp Asp Leu Ala Thr Ser Leu Val Leu
65                  70                  75                  80

Asp Pro Tyr Leu Gly Phe Gln Thr His Lys Met Asn Thr Ser Ala Phe
                85                  90                  95

Pro Ser Arg Ser Ser Arg His Phe Ser Lys Ser Asp Ser Phe Ser His
            100                 105                 110

Asn Asn Pro Val Arg Phe Arg Pro Ile Lys Gly Arg Gln Glu Glu Leu
        115                 120                 125

Lys Glu Val Ile Glu Arg Phe Lys Lys Asp Glu His Leu Glu Lys Ala
    130                 135                 140

Phe Lys Cys Leu Thr Ser Gly Glu Trp Ala Arg His Tyr Phe Leu Asn
145                 150                 155                 160

Lys Asn Lys Met Gln Glu Lys Leu Phe Lys Glu His Val Phe Ile Tyr
                165                 170                 175

Leu Arg Met Phe Ala Thr Asp Ser Gly Phe Glu Ile Leu Pro Cys Asn
            180                 185                 190
```

-continued

```
Arg Tyr Ser Ser Glu Gln Asn Gly Ala Lys Ile Val Ala Thr Lys Glu
            195                 200                 205

Trp Lys Arg Asn Asp Lys Ile Glu Leu Leu Val Gly Cys Ile Ala Glu
    210                 215                 220

Leu Ser Glu Ile Glu Glu Asn Met Leu Leu Arg His Gly Glu Asn Asp
225                 230                 235                 240

Phe Ser Val Met Tyr Ser Thr Arg Lys Asn Cys Ala Gln Leu Trp Leu
                245                 250                 255

Gly Pro Ala Ala Phe Ile Asn His Asp Cys Arg Pro Asn Cys Lys Phe
            260                 265                 270

Val Ser Thr Gly Arg Asp Thr Ala Cys Val Lys Ala Leu Arg Asp Ile
    275                 280                 285

Glu Pro Gly Glu Glu Ile Ser Cys Tyr Tyr Gly Asp Gly Phe Phe Gly
290                 295                 300

Glu Asn Asn Glu Phe Cys Glu Cys Tyr Thr Cys Glu Arg Arg Gly Thr
305                 310                 315                 320

Gly Ala Phe Lys Ser Arg Val Gly Leu Pro Ala Pro Ala Pro Val Ile
                325                 330                 335

Asn Ser Lys Tyr Gly Leu Arg Glu Thr Asp Lys Arg Leu Asn Arg Leu
            340                 345                 350

Lys Lys Leu Gly Asp Ser Ser Lys Asn Ser Asp Ser Gln Ser Val Ser
    355                 360                 365

Ser Asn Thr Asp Ala Asp Thr Thr Gln Glu Lys Asn Asn Ala Thr Ser
370                 375                 380

Asn Arg Lys Ser Ser Val Gly Val Lys Lys Asn Ser Lys Ser Arg Thr
385                 390                 395                 400

Leu Thr Arg Gln Ser Met Ser Arg Ile Pro Ala Ser Ser Asn Ser Thr
                405                 410                 415

Ser Ser Lys Leu Thr His Ile Asn Asn Ser Arg Val Pro Lys Lys Leu
            420                 425                 430

Lys Lys Pro Ala Lys Pro Leu Leu Ser Lys Ile Lys Leu Arg Asn His
    435                 440                 445

Cys Lys Arg Leu Glu Gln Lys Asn Ala Ser Arg Lys Leu Glu Met Gly
450                 455                 460

Asn Leu Val Leu Lys Glu Pro Lys Val Val Leu Tyr Lys Asn Leu Pro
465                 470                 475                 480

Ile Lys Lys Asp Lys Glu Pro Glu Gly Pro Ala Gln Ala Ala Val Ala
                485                 490                 495

Ser Gly Cys Leu Thr Arg His Ala Ala Arg Glu His Arg Gln Asn Pro
            500                 505                 510

Val Arg Gly Ala His Ser Gln Gly Glu Ser Ser Pro Cys Thr Tyr Ile
    515                 520                 525

Thr Arg Arg Ser Val Arg Thr Arg Thr Asn Leu Lys Glu Ala Ser Asp
530                 535                 540

Ile Lys Leu Glu Pro Asn Thr Leu Asn Gly Tyr Lys Ser Ser Val Thr
545                 550                 555                 560

Glu Pro Cys Pro Asp Ser Gly Glu Gln Leu Gln Pro Ala Pro Val Leu
                565                 570                 575

Gln Glu Glu Glu Leu Ala His Glu Thr Ala Gln Lys Gly Glu Ala Lys
            580                 585                 590

Cys His Lys Ser Asp Thr Gly Met Ser Lys Lys Ser Arg Gln Gly
    595                 600                 605
```

```
Lys Leu Val Lys Gln Phe Ala Lys Ile Glu Glu Ser Thr Pro Val His
        610                 615                 620

Asp Ser Pro Gly Lys Asp Ala Val Pro Asp Leu Met Gly Pro His
625                 630                 635                 640

Ser Asp Gln Gly Glu His Ser Gly Thr Val Gly Val Pro Val Ser Tyr
                645                 650                 655

Thr Asp Cys Ala Pro Ser Pro Val Gly Cys Ser Val Val Thr Ser Asp
            660                 665                 670

Ser Phe Lys Thr Lys Asp Ser Phe Arg Thr Ala Lys Ser Lys Lys Lys
        675                 680                 685

Arg Arg Ile Thr Arg Tyr Asp Ala Gln Leu Ile Leu Glu Asn Asn Ser
    690                 695                 700

Gly Ile Pro Lys Leu Thr Leu Arg Arg His Asp Ser Ser Lys
705                 710                 715                 720

Thr Asn Asp Gln Glu Asn Asp Gly Met Asn Ser Ser Lys Ile Ser Ile
                725                 730                 735

Lys Leu Ser Lys Asp His Asp Asn Asn Leu Tyr Val Ala Lys
                740                 745                 750

Leu Asn Asn Gly Phe Asn Ser Gly Ser Gly Ser Ser Thr Lys Leu
            755                 760                 765

Lys Ile Gln Leu Lys Arg Asp Glu Asn Arg Gly Ser Tyr Thr Glu
770                 775                 780

Gly Leu His Glu Asn Gly Val Cys Cys Ser Asp Pro Leu Ser Leu Leu
785                 790                 795                 800

Glu Ser Arg Met Glu Val Asp Asp Tyr Ser Gln Tyr Glu Glu Glu Ser
                805                 810                 815

Thr Asp Asp Ser Ser Ser Ser Glu Gly Asp Glu Glu Asp Asp Tyr
            820                 825                 830

Asp Asp Asp Phe Glu Asp Asp Phe Ile Pro Leu Pro Pro Ala Lys Arg
            835                 840                 845

Leu Arg Leu Ile Val Gly Lys Asp Ser Ile Asp Ile Ser Ser
    850                 855                 860

Arg Arg Arg Glu Asp Gln Ser Leu Arg Leu Asn Ala
865                 870                 875

<210> SEQ ID NO 15
<211> LENGTH: 120
<212> TYPE: PRT
<213> ORGANISM: Homo Sapiens
<220> FEATURE:
<221> NAME/KEY: SITE
<222> LOCATION: (1)..(120)
<223> OTHER INFORMATION: /note="SET domain of the AAP-4 protein,
      location 185-304"

<400> SEQUENCE: 15

Gly Phe Glu Ile Leu Pro Cys Asn Arg Tyr Ser Ser Glu Gln Asn Gly
1               5                   10                  15

Ala Lys Ile Val Ala Thr Lys Glu Trp Lys Arg Asn Asp Lys Ile Glu
            20                  25                  30

Leu Leu Val Gly Cys Ile Ala Glu Leu Ser Glu Ile Glu Glu Asn Met
        35                  40                  45

Leu Leu Arg His Gly Glu Asn Asp Phe Ser Val Met Tyr Ser Thr Arg
    50                  55                  60

Lys Asn Cys Ala Gln Leu Trp Leu Gly Pro Ala Ala Phe Ile Asn His
65                  70                  75                  80
```

```
                    -continued

Asp Cys Arg Pro Asn Cys Lys Phe Val Ser Thr Gly Arg Asp Thr Ala
                85                  90                  95

Cys Val Lys Ala Leu Arg Asp Ile Glu Pro Gly Glu Glu Ile Ser Cys
            100             105                 110

Tyr Tyr Gly Asp Gly Phe Phe Gly
        115             120
```